US011668712B2

(12) United States Patent
Lee et al.

(10) Patent No.: US 11,668,712 B2
(45) Date of Patent: Jun. 6, 2023

(54) ACCURATE, RAPID AND CONVENIENT SINGLE-STEP DISEASE DIAGNOSTIC METHOD USING SELF-AMPLIFICATION PRINCIPLE OF DETECTION SIGNAL

(71) Applicant: CELLEMEDY CO., LTD, Incheon (KR)

(72) Inventors: Jeewon Lee, Seoul (KR); Jeong-Hyeok Kwon, Seongnam-si (KR)

(73) Assignee: CELLEMEDY CO., LTD., Incheon (KR)

( * ) Notice: Subject to any disclaimer, the term of this patent is extended or adjusted under 35 U.S.C. 154(b) by 427 days.

(21) Appl. No.: 16/604,806

(22) PCT Filed: Apr. 13, 2018

(86) PCT No.: PCT/KR2018/004313
§ 371 (c)(1),
(2) Date: Oct. 11, 2019

(87) PCT Pub. No.: WO2018/190664
PCT Pub. Date: Oct. 18, 2018

(65) Prior Publication Data
US 2020/0124599 A1  Apr. 23, 2020

(30) Foreign Application Priority Data

Apr. 13, 2017  (KR) .................. 10-2017-0047841

(51) Int. Cl.
| | | |
|---|---|---|
| *G01N 33/53* | (2006.01) | |
| *G01N 33/553* | (2006.01) | |
| *G01N 33/52* | (2006.01) | |
| *G01N 33/569* | (2006.01) | |
| *G01N 33/68* | (2006.01) | |

(52) U.S. Cl.
CPC .......... *G01N 33/553* (2013.01); *G01N 33/52* (2013.01); *G01N 33/56988* (2013.01); *G01N 33/6893* (2013.01)

(58) Field of Classification Search
None
See application file for complete search history.

(56) References Cited

U.S. PATENT DOCUMENTS

| | | | | |
|---|---|---|---|---|
| 2006/0207388 A1* | 9/2006 | Mirkin | ..................... | C30B 29/60 75/371 |
| 2010/0279310 A1* | 11/2010 | Sia | ..................... | B01L 3/502707 435/7.1 |
| 2011/0275092 A1* | 11/2011 | Hu | ..................... | G01Q 60/34 435/7.1 |
| 2012/0134873 A1* | 5/2012 | Orner | ..................... | B22F 9/24 977/896 |
| 2016/0123968 A1* | 5/2016 | Iida | ..................... | C12Q 1/6834 506/9 |

FOREIGN PATENT DOCUMENTS

| | | |
|---|---|---|
| CN | 102449482 | 5/2012 |
| CN | 104726560 | 6/2015 |
| JP | 2005519620 | 7/2005 |
| JP | 2010529422 | 8/2010 |
| JP | 2011510909 | 4/2011 |
| JP | 2012529644 | 11/2012 |
| JP | 2017037014 | 2/2017 |
| KR | 10-2010-0128550 | 12/2010 |
| KR | 10-2011-0090347 | 8/2011 |
| KR | 10-2012-0067967 | 6/2012 |
| KR | 20140133478 | 11/2014 |
| KR | 10-1495665 | 2/2015 |
| KR | 10-2014-0151305 | 5/2016 |
| KR | 10-2016-0051393 | 5/2016 |
| KR | 10-2016-0061304 | 5/2016 |
| KR | 10-2016-0117688 | 10/2016 |
| KR | 10-2017-0023589 | 3/2017 |
| WO | WO 1988/007085 | 9/1988 |
| WO | WO 1988/007086 | 9/1988 |
| WO | WO 1988/009344 | 12/1988 |

OTHER PUBLICATIONS

Choo, et al., "Isolation of a cDNA Clone Derived from a Blood-Borne non-A, non-B Viral Hepatitis Genome," *Science*, 244:359-362, 1989.
Darwish, "Immunoassay Methods and Their Applications in Pharmaceutical Analysis: Basic Methodology and Recent Advances," *International Journal of Biomedical Science*, 2: 217-235, 2006.
International Search Report and Written Opinion Issued in Corresponding PCT Patent Application No. PCT/KR2018/004313, dated Sep. 3, 2018.
Rosenberg, "Recent Advances in the Molecular Biology of Hepatitis C Virus," *Journal of Molecular Biology*, 313: 451-464, 2001.
Scaglioni, et al., "Recent Advances in the Molecular Biology of Hepatitis B Virus," *Bailliere's Clinical Gastroenterology*, 10(2): 207-225, 1996.
Shah, "Enzyme-Linked Immunosorbent Assay (ELISA): The Basics," *British Journal of Hospital Medicine*, 77(7): C98-C101, 2016.
Vogesser, et al., "Multicenter Analytical Evaluation of the Automated Electrochemiluminescence Immunoassay for Cyclosporine," *Therapeutic Drug Monitoring*, 36(5): 640-650, 2014.

(Continued)

*Primary Examiner* — Gary Counts
(74) *Attorney, Agent, or Firm* — Norton Rose Fulbright US LLP

(57) ABSTRACT

A method for detecting a disease marker using self-amplification of a detection signal is disclosed. The method can include (a) a step of simultaneously inducing an antigen-antibody immune response and an Au particle formation reaction by reduction of Au ions in an assay solution prepared by, to a pre-assay solution in which all of an antibody or antigen for detection of a disease-specific marker, free Au ions, and adsorbed Au ions are present, adding a sample, which contains a disease-specific antigen or antibody binding specifically to the antibody or the antigen, and a reducing agent; and (b) a step of confirming the presence or absence of a disease-specific marker by a chromogenic reaction through the Au particle formation.

14 Claims, 27 Drawing Sheets
Specification includes a Sequence Listing.

(56) References Cited

OTHER PUBLICATIONS

Extended European Search Report issued in Corresponding European Application No. 18784065.7, dated Nov. 20, 2020.
Kwon et al., "Signal self-enhancement by coordinated assembly of gold nanoparticles enables accurate one-step-immunoassays" *Nanoscale* 2017, 9, 16476-16484.
Office Action issued in Corresponding Japanese Application No. 2020-506696, dated Nov. 10, 2020 (English Translation provided).
Office action issued in Corresponding Chinese Application No. 201880025139.8, dated Jul. 4, 2022 (English Translation provided).

\* cited by examiner (A)

(B)

| Standard conc. | ELISA (Mean ± s.d.) |
|---|---|
| 30 ng/ml | 70.81 ± 4.31 ng/ml |
| 20 ng/ml | 38.70 ± 4.58 ng/ml |
| 10 ng/ml | 14.84 ± 1.25 ng/ml |
| 5 ng/ml | 9.70 ± 0.86 ng/ml |
| 2 ng/ml | 5.11 ± 2.10 ng/ml |
| 0 ng/ml | 0.57 ± 0.51 ng/ml |

| Standard conc. | ELISA (Mean ± sd) |
|---|---|
| 30 ng/ml | 63.15 ± 5.51 ng/ml |
| 20 ng/ml | 39.36 ± 7.16 ng/ml |
| 10 ng/ml | 23.84 ± 5.85 ng/ml |
| 5 ng/ml | 10.24 ± 0.84 ng/ml |
| 2 ng/ml | 7.77 ± 2.58 ng/ml |
| 0 ng/ml | 0.51 ± 0.65 ng/ml |

SEQUENCE LISTING

```
<160> NUMBER OF SEQ ID NOS: 16

<210> SEQ ID NO 1
<211> LENGTH: 24
<212> TYPE: DNA
<213> ORGANISM: Artificial Sequence
<220> FEATURE:
<223> OTHER INFORMATION: Synthetic nucleic acid - H6-SPAB-capsid_F

<400> SEQUENCE: 1
ctcgaggcac cgaaagctga taac                                              24

<210> SEQ ID NO 2
<211> LENGTH: 24
<212> TYPE: DNA
<213> ORGANISM: Artificial Sequence
<220> FEATURE:
<223> OTHER INFORMATION: Synthetic nucleic acid - H6-SPAB-capsid_R

<400> SEQUENCE: 2
ggatccgtca gcttttagtg cttg                                              24

<210> SEQ ID NO 3
<211> LENGTH: 24
<212> TYPE: DNA
<213> ORGANISM: Artificial Sequence
<220> FEATURE:
<223> OTHER INFORMATION: Synthetic nucleic acid - H6-c33c-capsid_F

<400> SEQUENCE: 3
ctcgaggcgg tggactttat ccct                                              24

<210> SEQ ID NO 4
<211> LENGTH: 24
<212> TYPE: DNA
<213> ORGANISM: Artificial Sequence
<220> FEATURE:
<223> OTHER INFORMATION: Synthetic nucleic acid - H6-c33c-capsid_R

<400> SEQUENCE: 4
ggatccacac gtattgcagt ctat                                              24

<210> SEQ ID NO 5
<211> LENGTH: 24
<212> TYPE: DNA
<213> ORGANISM: Artificial Sequence
<220> FEATURE:
<223> OTHER INFORMATION: Synthetic nucleic acid - H6-gp41-capsid_F

<400> SEQUENCE: 5
ctcgagatcc tggctgtgga acgc                                              24
```

-continued

```
<210> SEQ ID NO 6
<211> LENGTH: 24
<212> TYPE: DNA
<213> ORGANISM: Artificial Sequence
<220> FEATURE:
<223> OTHER INFORMATION: Synthetic nucleic acid - H6-gp41-capsid_R

<400> SEQUENCE: 6
ggatccgatc aactttccac tagc                                          24

<210> SEQ ID NO 7
<211> LENGTH: 24
<212> TYPE: DNA
<213> ORGANISM: Artificial Sequence
<220> FEATURE:
<223> OTHER INFORMATION: Synthetic nucleic acid - H6-p24-capsid_F

<400> SEQUENCE: 7
ctcgagccgg aagtaatccc gatg                                          24

<210> SEQ ID NO 8
<211> LENGTH: 24
<212> TYPE: DNA
<213> ORGANISM: Artificial Sequence
<220> FEATURE:
<223> OTHER INFORMATION: Synthetic nucleic acid - H6-p24-capsid_R

<400> SEQUENCE: 8
ggatcctccc actccctgac atgc                                          24

<210> SEQ ID NO 9
<211> LENGTH: 24
<212> TYPE: DNA
<213> ORGANISM: Artificial Sequence
<220> FEATURE:
<223> OTHER INFORMATION: Synthetic nucleic acid - hFTN-511p-c100p-c22p-
      H6_F

<400> SEQUENCE: 9
ctcgagatca tccccgatag ggaa                                          24

<210> SEQ ID NO 10
<211> LENGTH: 24
<212> TYPE: DNA
<213> ORGANISM: Artificial Sequence
<220> FEATURE:
<223> OTHER INFORMATION: Synthetic nucleic acid - hFTN-511p-c100p-c22p-
      H6_R

<400> SEQUENCE: 10
ggatccggaa gtcttcctag tcgc                                          24

<210> SEQ ID NO 11
<211> LENGTH: 21
<212> TYPE: DNA
<213> ORGANISM: Artificial Sequence
<220> FEATURE:
<223> OTHER INFORMATION: Synthetic nucleic acid - hFTN-ep1-H6_F

<400> SEQUENCE: 11
ctcgaggaac ctttgagaac c                                             21

<210> SEQ ID NO 12
<211> LENGTH: 21
<212> TYPE: DNA
<213> ORGANISM: Artificial Sequence
<220> FEATURE:
```

-continued

```
<223> OTHER INFORMATION: Synthetic nucleic acid - hFTN-ep1-H6_R

<400> SEQUENCE: 12
gaattctttc ctaggaggtg g                                         21

<210> SEQ ID NO 13
<211> LENGTH: 21
<212> TYPE: DNA
<213> ORGANISM: Artificial Sequence
<220> FEATURE:
<223> OTHER INFORMATION: Synthetic nucleic acid - hFTN-ep2-H6_F

<400> SEQUENCE: 13
ctcgagaaaa tcaatttggc a                                         21

<210> SEQ ID NO 14
<211> LENGTH: 21
<212> TYPE: DNA
<213> ORGANISM: Artificial Sequence
<220> FEATURE:
<223> OTHER INFORMATION: Synthetic nucleic acid - hFTN-ep2-H6_R

<400> SEQUENCE: 14
gaattcctga ctttcaattt t                                         21

<210> SEQ ID NO 15
<211> LENGTH: 21
<212> TYPE: DNA
<213> ORGANISM: Artificial Sequence
<220> FEATURE:
<223> OTHER INFORMATION: Synthetic nucleic acid - hFTN-ep3-H6_F

<400> SEQUENCE: 15
catatgacga ccgcgtccac c                                         21

<210> SEQ ID NO 16
<211> LENGTH: 21
<212> TYPE: DNA
<213> ORGANISM: Artificial Sequence
<220> FEATURE:
<223> OTHER INFORMATION: Synthetic nucleic acid - hFTN-ep3-H6_R

<400> SEQUENCE: 16
atcgatttag tgatggtgat g                                         21
```

ACCURATE, RAPID AND CONVENIENT SINGLE-STEP DISEASE DIAGNOSTIC METHOD USING SELF-AMPLIFICATION PRINCIPLE OF DETECTION SIGNAL

CROSS-REFERENCE TO RELATED APPLICATIONS

This application is a national phase application under 35 U.S.C. § 371 of International Application No. PCT/KR2018/004313, filed Apr. 13, 2018, which claims priority to and the benefit of Korean Patent Application No. 10-2017-0047841, filed Apr. 13, 2017. The contents of the referenced patent applications are incorporated into the present application by reference.

FIELD OF THE DISCLOSURE

The present invention relates to a method of accurately, rapidly, and conveniently detecting a disease marker by linking immunodiagnostics and Au particle formation at the same time and, accordingly, realizing self-amplification of a detection signal and a kit therefor, more particularly, to a method of detecting a disease-specific marker using self-amplification of a detection signal and a kit therefor, the method including (a) a step of simultaneously inducing an antigen-antibody immune response and an Au particle formation reaction by reduction of Au ions in an assay solution prepared by, to a pre-assay solution in which all of an antibody or antigen for detection of a disease-specific marker, free Au ions, and adsorbed Au ions are present, adding a sample, which contains a disease-specific antigen or antibody binding specifically to the antibody or the antigen, and a reducing agent; and (b) a step of confirming the presence or absence of a disease-specific marker by a chromogenic reaction through the Au particle formation.

DESCRIPTION OF RELATED ART

In modern disease diagnosis, a diagnosis method having a rapid, accurate and simple procedure is most ideal. In addition, such rapid diagnosis is more important in patients with emergencies such as acute myocardial infarction. This rapid diagnosis is more important in patients with emergencies such as acute myocardial infarction. In the case of emergency patients, proper treatment according to rapid and accurate diagnosis is more important than the case of non-emergency patients because it is directly related to survival thereof.

In the field of clinical examination, the diagnosis of various diseases is performed using biological samples (blood, urine, etc.). As such a diagnosis method, various measurement methods have been developed and used. As representative methods of the measurement methods, there are biochemical assays using enzyme reactions and immunoassays using antigen-antibody reactions. Recently, it has been required to accurately measure components in biological samples. Accordingly, immunoassay methods using an antigen-antibody reaction with high specificity have been widely used.

Immunoassay methods utilize binding ability between an antigen and an antibody. Immunoassays are mainly used to analyze the presence of a specific antigen (or antibody)-a specific antibody (or antigen) in a sample. In particular, immunoassays are performed by flowing a sample on a specific antigen (or antibody) immobilized on a solid support (followed by washing), and then visualizing a bound antibody (or antigen) using various techniques.

In immunoassay methods, calibrators are generally used to determine (assign) the concentration of an unknown sample. In classical immunoassay, a set of calibrators is used, a calibration curve of a signal versus concentration is plotted, and the concentration of an unknown sample is determined by interpolation (Ibrahim A. Darwish, International Journal of Biomedical Science, Vol. 2 pp. 217-235, 2006).

Immunoassays can be classified into radioimmunoassay (RIA) in which signals are detected using radioisotopes, enzyme-linked immunosorbent assay (ELISA) or enzyme immunoassay (EIA) using signal amplification by an enzyme, a fluorescence antibody technique (FA) using fluorescence detection, chemiluminescence immunoassay (CLIA) using chemiluminescence, etc. according to the principle of detection and a method thereof. In addition, various classifications can be made according to use methods of labeling substances and substrate types.

ELISA can be greatly classified into direct ELISA, indirect ELISA, sandwich ELISA, and competitive ELISA.

Direct ELISA involves immobilizing an antigen on a 96-well plate, etc., and then injecting an enzyme-binding antibody thereto to cause an antigen-antibody reaction, followed by a washing process so as to measure the amount of a product converted from a substrate by the enzyme attached to the antibody. This method has the advantage of being faster than other ELISAs, but it is disadvantageous in that sensitivity is low, a specific antibody for each ELISA is required, it takes a long time, and costs are high.

Indirect ELISA involves immobilizing an antigen to a 96-well plate, and then treating with a primary antibody to induce an antigen-antibody reaction, followed by treating with an enzyme-bound secondary antibody so as to bind to an Fc domain of the primary antibody, followed by measuring the amount of a product converted from a substrate by the enzyme. This method has advantages such as high sensitivity, relative inexpensiveness, and the use of various types of primary antibodies, but it is disadvantageous in that the possibility of a false positive reaction due to cross-reaction between secondary antibodies is high, process steps are complicated, and it takes a long time.

Sandwich ELISA involves immobilizing a capture antibody capable of binding to an antigen to a 96-well plate, and then injecting a sample containing the antigen and injecting a detection antibody capable of binding another epitope of the antigen such that a sandwich structure of the capture antibody-antigen-detection antibody can be combined with an Fc domain of the detection antibody and, accordingly, an enzyme-bound secondary antibody can be detected. This method is advantageous in that a sample preparation step can be minimized and high sensitivity and accuracy are provided, but it is disadvantageous in that primary and secondary antibodies should be prepared to bind to different epitopes of the antigen, it takes a long time, and costs are high.

Competitive ELISA involves injecting an antibody into a sample to induce an antigen-antibody reaction, and then injecting the antigen-antibody complex into an antigen-coated 96-well plate, followed by injecting an enzyme-bound secondary antibody to measure the amount of a product converted from a substrate. In the case of this method, the amount of a product converted by a secondary antibody is decreased with increasing amount of an antigen present in a sample. This method is advantageous in that a sample preparation step can be minimized, a wide range of antigen amounts can be measured, and even small epitopes, such as small molecules, can be detected, but it is disadvantageous in that it can be applied to diluted samples (Karichma Sha et al., British Journal of Hospital Medicine, Vol. 77, No. 7, 2016).

Electro-chemiluminescent (ECL) reaction is a chemiluminescence reaction occurring on a surface of an electrode induced by an electrochemical reaction. In particular, a conjugate of an antigen-antibody complex and ruthenium pyridine is excited by an electrochemical reaction in the presence of tripropylamine, and a redox reaction occurs to emit photons. The emitted photons may be collected by a photomultiplier tube. This process is repeatedly performed to generate photons, which amplifies optical signals. For electrochemiluminescence analysis, labels capable of binding to an antibody or antigen having a different chemical structure are generally used to produce a labeled antibody or antigen (Michael Vogesser et al., Ther. Drug Monit. Vol. 36, No. 5, pp. 640-650, 2014).

The ELISA method has advantages such as high sensitivity, a fast analysis speed, and easy automation, but it is disadvantageous in that several steps should be included and manufacturing costs of a labeled antibody or antigen are high. In the case of ruthenium pyridine, which is generally used, the properties thereof are greatly affected by an electrode material type, and there are disadvantageous such as limited luminous efficiency and high costs.

To overcome the disadvantages, Korean Patent No. 10-1495665 has developed a fluorescence multiple immunoassay using a magnetic. However, this method also includes several steps, thereby taking a long time. Korean Patent No. 10-2014-0151305 has developed a method of increasing sensitivity by using protein particles such that an antigen is exposed while having correct orientation on a surface of the protein particles. However, this method also includes several steps and takes a long time. Accordingly, there is a need for an easy and rapid detection method.

Therefore, the present inventors have made diligent efforts to improve the disadvantages of existing immunoassay methods. As a result, the present inventors confirmed that, when Au particle formation using reduction of Au ions and an antigen-antibody immune response are simultaneously induced, a detection signal self-amplifies according to formation of aggregates of Au particles, which allows rapid detection of the presence or absence of a disease-specific marker, thus completing the present invention.

The above information described in this Background section is only provided to improve the understanding of the background of the present invention, and thus, information on prior art that is known to those of ordinary skill in the art may be excluded.

SUMMARY OF THE INVENTION

Therefore, the present invention has been made in view of the above problems, and it is one object of the present invention to provide a method of accurately, rapidly, and conveniently detecting a disease-specific marker in a single step using a self-amplification principle of a detection signal.

In accordance with an aspect of the present invention, the above and other objects can be accomplished by the provision of a method of detecting a disease-specific marker using self-amplification of a detection signal, the method including: (a) a step of simultaneously inducing an antigen-antibody immune response and an Au particle formation reaction by reduction of Au ions in an assay solution prepared by, to a pre-assay solution in which all of an antibody or antigen for detection of a disease-specific marker, free Au ions, and adsorbed Au ions are present, adding a sample, which contains a disease-specific antigen or antibody binding specifically to the antibody or the antigen, and a reducing agent; and (b) a step of confirming the presence or absence of a disease-specific marker by a chromogenic reaction through the Au particle formation.

In accordance with another aspect of the present invention, there is provided a method of detecting an antiviral antibody using self-amplification of a detection signal, the method including: (a) a step of simultaneously inducing an antigen-antibody immune response and an Au particle formation reaction by reduction of Au ions in an assay solution prepared by, to a pre-assay solution in which all of an antigen for detecting an antiviral antibody, free Au ions, and adsorbed Au ions are present, adding a sample, which contains an antiviral antibody binding specifically to the antigen, and a reducing agent; and (b) a step of confirming the presence or absence of virus by a chromogenic reaction through the Au particle formation.

In accordance with another aspect of the present invention, there is provided a method of providing information for disease diagnosis using detection signal self-amplification, the method including: (a) a step of simultaneously inducing an antigen-antibody immune response and an Au particle formation reaction by reduction of Au ions in an assay solution prepared by, to a pre-assay solution in which all of an antibody or antigen for detection of a disease-specific marker, free Au ions, and adsorbed Au ions are present, adding a sample, which contains a disease-specific antigen or antibody binding specifically to the antibody or the antigen, and a reducing agent; and (b) a step of confirming the presence or absence of a disease-specific marker by a chromogenic reaction through the Au particle formation.

In accordance with yet another aspect of the present invention, there is provided a method of diagnosing a disease using detection signal self-amplification, the method including: (a) a step of simultaneously inducing an antigen-antibody immune response and an Au particle formation reaction by reduction of Au ions in an assay solution prepared by, to a pre-assay solution in which all of an antibody or antigen for detection of a disease-specific marker, free Au ions, and adsorbed Au ions are present, adding a sample, which contains a disease-specific antigen or antibody binding specifically to the antibody or the antigen, and a reducing agent; and (b) a step of confirming the presence or absence of a disease-specific marker by a chromogenic reaction through the Au particle formation.

BRIEF DESCRIPTION OF THE DRAWINGS

FIG. 14 illustrates an analysis result of a normal individual sample (A), FIG. 15 illustrates an analysis result of a normal individual sample (B), and FIG. 16 illustrates an analysis result of a normal individual sample (C).

FIG. 17 illustrates an analysis result of a normal individual sample (A), FIG. 18 illustrates an analysis result of a normal individual sample (B), and FIG. 19 illustrates an analysis result of a normal individual sample (C).

FIG. 20 illustrates an analysis result of a normal individual sample (A), FIG. 21 illustrates an analysis result of a normal individual sample (B), and FIG. 22 illustrates an analysis result of a normal individual sample (C).

FIG. 23 illustrates an analysis result of a normal individual sample (A), FIG. 24 illustrates an analysis result of a normal individual sample (B), and FIG. 25 illustrates an analysis result of a normal individual sample (C).

DETAILED DESCRIPTION OF THE INVENTION

Unless otherwise defined, all terms including technical and scientific terms used herein have the same meaning as commonly understood by one of ordinary skill in the art to which this inventive concept belongs. In general, nomenclature used in the present specification is well known and commonly used in the art.

The present invention has been made to confirm whether self-amplification of a detection signal according to an antigen-antibody immune response and Au particle formation due to reduction of Au ions occurs in an assay solution prepared by, to a pre-assay solution in which all of an antibody or antigen for detection of a disease-specific marker, free Au ions, and adsorbed Au ions are present, adding a sample, which contains a disease-specific antigen or antibody binding specifically to the antibody or the antigen, and a reducing agent, and thus, it is possible to detect a disease-specific marker.

According to the present invention, protein particles wherein a tag for gold ion adsorption and a tag for binding an antibody Fc domain are exposed from a surface of a recombinant hepatitis B virus capsid (HBV-capsid)-derived core protein were prepared, and then an antibody capable of detecting a maker for acute myocardial infarction was attached to surfaces of the protein particles, and then an aqueous solution including the protein particles to which Au ions were absorbed was prepared. A marker for acute myocardial infarction and a reducing agent were added to the aqueous solution and, after 5 minutes, a chromogenic reaction was observed by the naked eye.

Figure 1:
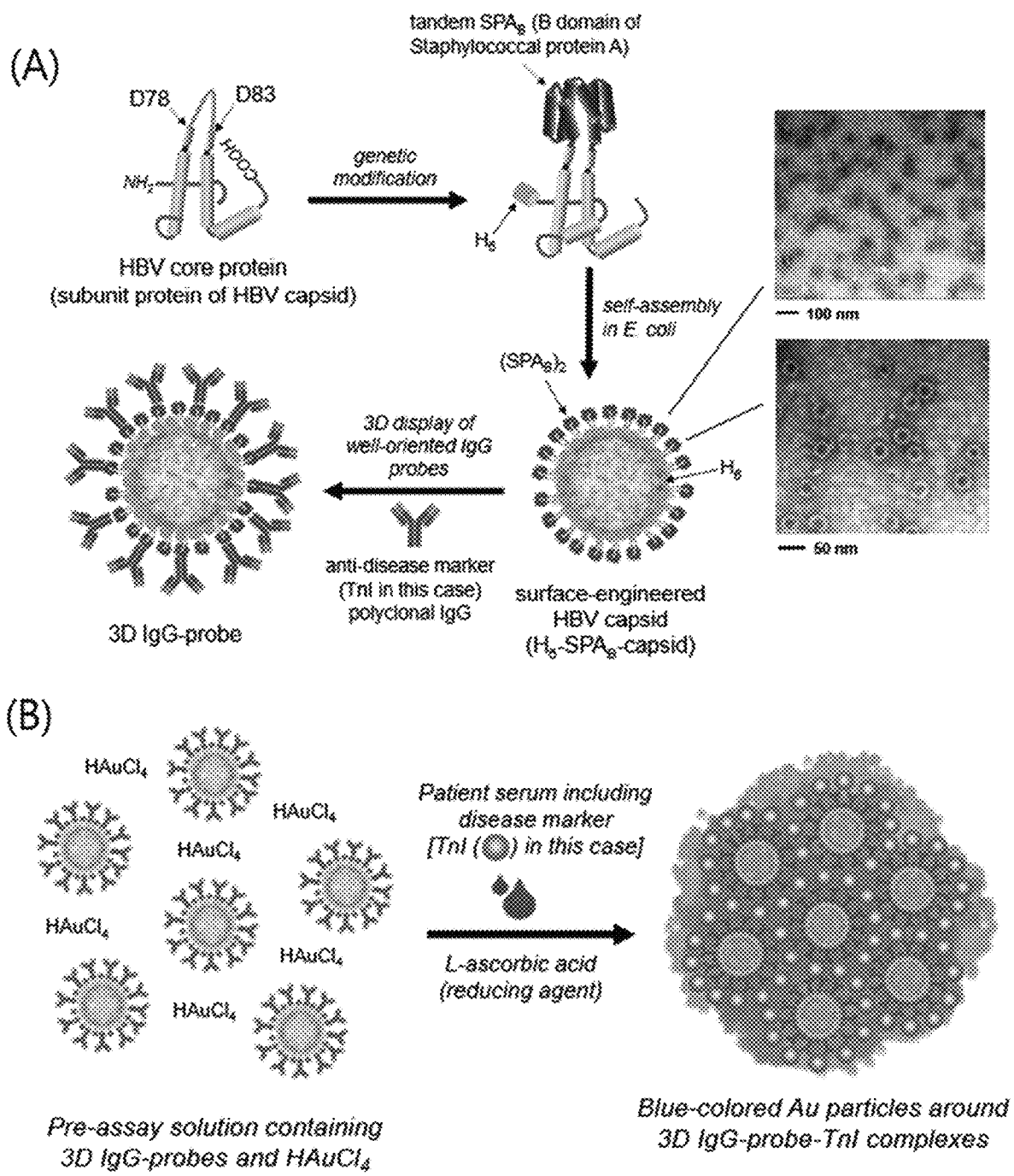
FIG. 1(A) illustrates a schematic diagram of protein particles for the diagnosis of acute myocardial infarction according to a method of the present invention and electron micrographs of the generated protein particles.
FIG. 1(B) is a schematic diagram illustrating a principle of the present invention, particularly a process in which Au particle formation and an antigen-antibody reaction simultaneously occur and thus a cluster is formed, so that rapid self-signal amplification occurs.

That is, according to an embodiment of the present invention, a hexa-histidine capable of adsorbing Au ions is expressed at an N-terminal of an HBV core protein, and a linker amino acid and a B domain of Staphylococcal Protein A capable of binding to an Fc domain of an antibody were bound to a loop portion, thereby preparing surface-modified recombinant HBV capsid protein particles (FIG. 1).

Figure 2:
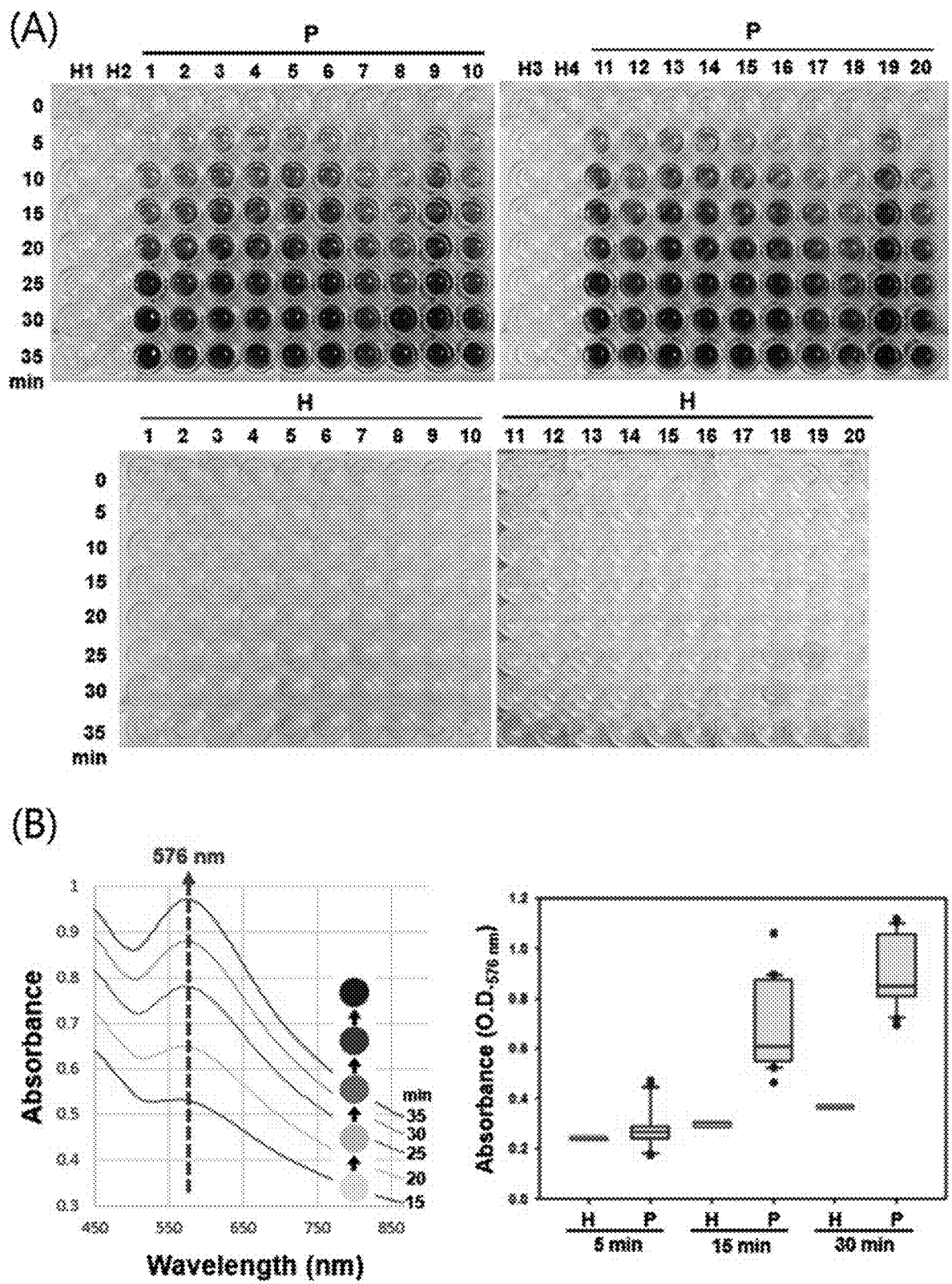
FIG. 2(A) illustrates one-step diagnosis results of serum of a patient with acute myocardial infarction and serum of a normal individual.
FIG. 2(B) illustrates experimental results showing that color changes in the sample of the patient with myocardial infarction are due to a difference in an absorbance of absorbing light at a specific wavelength, and an absorbance level difference between the patient and the normal individual at each time.

An antibody of troponin I (TnI) that is overexpressed in the case of acute myocardial infarction was bound to the protein particles to prepare protein particles in which an antibody was correctly oriented, and then a patient blood sample containing L-ascorbic acid (LAA) and TnI was injected thereto to induce an aggregation reaction (FIG. 1 B). As a result, it was confirmed that, after 5 minutes, a chromogenic reaction observable by the naked eye occurred in the patient sample (FIG. 2).

Accordingly, in an aspect of the present invention, the present invention relates to a method of detecting a disease-specific marker using self-amplification of a detection signal, the method including (a) a step of simultaneously inducing an antigen-antibody immune response and an Au particle formation reaction by reduction of Au ions in an assay solution prepared by, to a pre-assay solution in which all of an antibody or antigen for detection of a disease-specific marker, free Au ions, and adsorbed Au ions are present, adding a sample, which contains a disease-specific antigen or antibody binding specifically to the antibody or the antigen, and a reducing agent; and (b) a step of confirming the presence or absence of a disease-specific marker by a chromogenic reaction through the Au particle formation.

The term "pre-assay solution" used in the present invention refers to a solution including an antibody (or an antigen) specifically binding to adsorbed Au ions, free Au ions, and an antigen (or an antibody) to be detected. The pre-assay solution may further include other buffers according to reaction conditions, particles from which amino acids adsorbing an antibody or an antigen and Au ions are exposed, and the like.

The term "assay solution" used in the present invention refers to a solution prepared by adding a sample and a reducing agent to the pre-assay solution. The sample may include an antigen or antibody to be detected.

The term "antibody" used in the present invention refers to an immunoglobulin selected from the group consisting of IgA, IgE, IgM, IgD, IgY and IgG. An antibody may specifically bind to a target antigen. An antibody is composed of two light chains and two heavy chains. Each of the chains is composed of a variable domain, an amino acid sequence of which is variable, and a constant domain, an amino acid sequence of which is constant. A site to which an antigen is bound is located at an end of a three-dimensional structure of a variable domain. The site is formed by a group of complementarity determining regions in which three light chains and three heavy chains are present. In a variable domain, the complementarity determining regions have highly variable amino acid sequences. Due to such high variability, an antibody specific to various antigens can be found. The scope of the present invention includes a complete antibody form and an antigen-binding fragment of the antibody molecule.

The term "single-chain Fv (ScFv, a single-chain fragment antibody or an antibody fragment)" used in the present invention refers to an antibody formed by connecting variable domains of a light chain and heavy chain to each other. As needed, a linker consisting of a peptide chain formed by connecting about 15 amino acids may be included. Here, ScFv may have a structure of a variable domain of a light chain-a linker-a variable domain of a heavy chain or a structure of a variable domain of a heavy chain-a linker-a variable domain of a light chain, and has antigen specificity the same as or similar to that of the original antibody.

A complete antibody includes two full-length light chains and two full-length heavy chains, and each of the light chains is connected to the heavy chain by a disulfide bond. A constant region of the heavy chain belongs to gamma (γ), mu (μ), alpha (α), delta (δ), and epsilon (ε) types and, as subclasses, includes gamma 1 (γ1), gamma 2 (γ2), gamma 3 (γ3), gamma 4 (γ4), alpha 1 (α1 ) and alpha 2 (α2). A constant region of the light chain belongs to kappa (κ) and lambda (λ) types.

An antigen-binding fragment of an antibody or an antibody fragment refers to a fragment having an antigen-binding function, and includes Fab, F(ab'), F(ab')2, Fv, and the like. Fab among antibody fragments has variable domains of light and heavy chains, a constant region of a light chain, and a first constant region (CH1) of a heavy chain, and one antigen-binding site. Fab' is different from Fab in that Fab' has a hinge region wherein one or more cysteine residues are present at a C-terminal of a heavy chain CH1 domain. An antibody of F(ab')2 is generated by a disulfide bond of cysteine residues at hinge regions of Fab'. Fv is a minimum antibody fragment only having a heavy-chain variable domain and a light-chain variable domain. Recombination techniques for producing Fv fragments are disclosed in PCT International Publication Nos. WO88/10649, WO88/106630, WO88/07085, WO88/07086, and WO88/09344. In the case of two-chain Fv, a heavy-chain variable domain and a light-chain variable domain are connected to each other by a non-covalent bond. In the case of single-chain Fv (scFv), a variable domain of a heavy chain and a variable domain of a light chain are connected to each other by a covalent bond through a peptide linker, or direct connection at a C-terminal is made, thereby forming a dimer structure such as two-chain Fv. Such antibody fragments can be obtained using a protein hydrolase (for example, Fab can be obtained by restriction-digesting an entire antibody with papain, and a F(ab')2 fragment can be obtained by digesting with pepsin) or using a gene recombination technique.

Examples of the antibody of the present invention include a monoclonal antibody, a multispecific antibody, a human antibody, a humanized antibody, a chimeric antibody, a single-chain Fvs (scFV), a single-chain antibody, a Fab fragment, a F(ab') fragment, disulfide-binding Fvs (sdFV), an anti-idiotype (anti-Id) antibody, an epitope-binding fragment of the antibody, and the like, but the present invention is not limited thereto.

In the present invention, the adsorbed Au ions may be any one adsorbed to a material capable of adsorbing Au ions, preferably a material capable of being adsorbed to amino acids, more preferably a material capable of being adsorbed to an amino acid selected from the group consisting of histidine, lysine and arginine, but the present invention is not limited thereto.

In the present invention, the reducing agent may be any material capable of reducing Au ions into Au particles under reaction conditions of the present invention, preferably may be selected from the group consisting of ascorbic acid, imidazole, pyrazole, histamine, hydroxyl amine, citric acid, and sodium borohydride.

In the present invention, the sample may be selected from the group consisting of blood, plasma, serum, urine, saliva, oral mucosa, and saliva, but the present invention is not limited thereto.

In the present invention, the concentration of the Au ions (free Au ions +adsorbed Au ions) present in the pre-assay solution may be 1 mM to 10 mM, but the present invention is not limited thereto.

In the present invention, the concentration of the reducing agent present in the assay solution may be 0.005 M to 0.1 M, but the present invention is not limited thereto.

In the present invention, the amount of the sample may be 10 μl to 30 μl, but the present invention is not limited thereto.

In the present invention, when the concentration of the Au ions, the concentration of the reducing agent, and the amount of the sample are smaller than reference values, effective disease marker detection may not be performed. When the concentration of the Au ions, the concentration of the reducing agent, and the amount of the sample are greater than reference values, negative effects such as a false positive effect may be exhibited.

In the present invention, in the case of an antigen or antibody for detecting the disease-specific marker, the antigen or the antibody may be exposed form surfaces of protein particles. From the surfaces of the protein particles, a tag selected from the group consisting of histidine, lysine, and arginine capable of adsorbing Au ions may be further exposed.

In the present invention, an immune response of the antigen or antibody for detecting the disease-specific marker may occur on surfaces of protein particles. The tag may adsorb Au ions to induce aggregation of Au particles in the presence of a reducing agent.

In the present invention, the protein particles may be any particles formed by a self-assembly function of a protein, preferably may be selected from the group consisting of ferritin, ferritin-like proteins, magnetosome-constituting proteins, virus-constituting proteins (e.g. hepatitis B virus core protein, tobacco mosaic virus) DNA binding proteins (DPS), and proteasomes, but the present invention is not limited thereto. In the present invention, the virus-constituting proteins may be selected from the group consisting of capsid proteins of human hepatitis B virus.

In the present invention, the sizes of the protein particles may be 10 nm to 50 nm, but the present invention is not limited thereto.

In the present invention, in the case of the antibody for detecting a disease-specific marker exposed from surfaces of the protein particles, a domain capable of binding to an Fc domain of the antibody is exposed from surfaces of the protein particles, whereby the domain may bind to the antibody for detecting the disease-specific marker.

In the present invention, a domain capable of binding to the Fc domain of the antibody may be selected from the group consisting of B domain of Staphylococcal protein A and protein G, but the present invention is not limited thereto.

In the present invention, a domain capable of binding to the Fc domain of the antibody is exposed from surfaces of the protein particles. Such exposure may be further effectively made due to a linker protein.

In the present invention, the linker protein is not specifically limited so long as it is an amino acid capable of effectively exposing a domain, capable of binding to the Fc domain of the antibody, from surfaces of protein particles, and, preferably, may be G4SG4T or G4S G4.

In the present invention, the chromogenic reaction may more rapidly occur in a group, to which a sample of a patient is added, than a group to which a normal sample is added. In the patient group, the chromogenic reaction occurs within a minimum of 5 minutes to a maximum of 10 minutes. However, a reaction time may be changed according to reaction conditions.

In the present invention, the chromogenic reaction may be detected using any method of detecting changes in visible light and, preferably, may be detected by the naked eye or using a spectrophotometer, and an absorbance may be detected at 500 to 600 nm, but the present invention is not limited thereto.

In the present invention, by self-amplification of a detection signal, a small amount of disease marker is detected and a resultant result is expressed by a color change that can be observed by the naked eye. Such self-amplification of a signal is caused by a phenomenon that Au ions dissolved in a solution for diagnosis are reduced into Au particles by a reducing agent. As the sizes of Au particles increase, a resultant color change is expressed as a signal that can be confirmed by the naked eye.

In the case of protein particles used in the present invention, hexa-histidine is fused to and expressed in monomers thereof. Here, since histidine amino acids have a property of binding with Au ions, Au ions bound to aggregates generated due to an antigen-antibody reaction react with a reducing agent, thereby being reduced into Au particles. The sizes of the Au particles increase as other Au ions are reduced, thereby forming larger Au particles. Such resultant aggregates are colored.

In the case of a normal individual serum, an antigen-antibody reaction does not occur. Accordingly, a generation speed of aggregates due to Au particles is low, whereby a time taken until a color is expressed is significantly slow. Through such color change, a patient may be distinguished from a normal individual.

In the present invention, whether a virus can be detected using self-amplification of a detection signal was also investigated.

Figure 8:
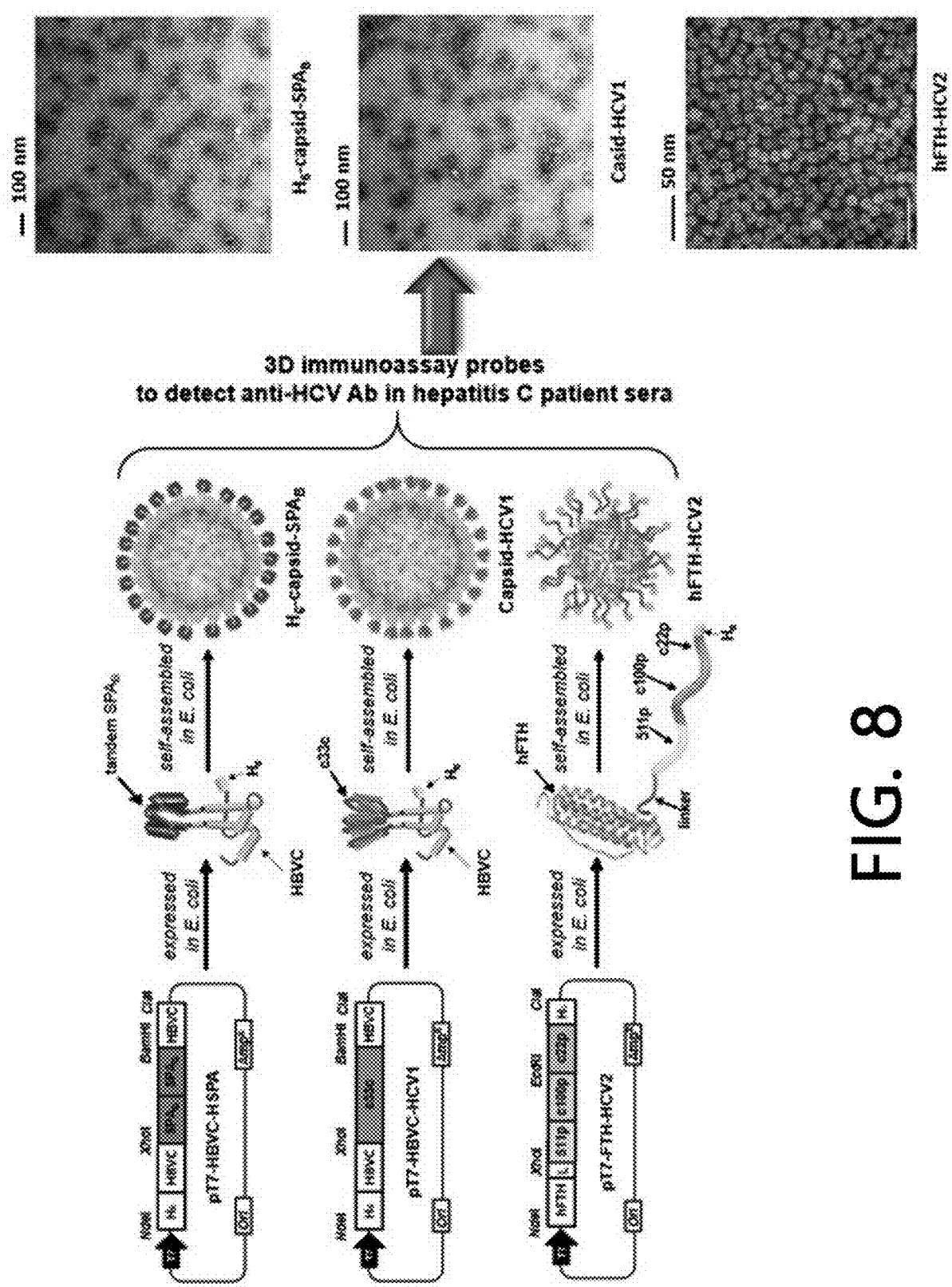
FIG. 8 illustrates schematic diagrams of protein particles prepared to diagnose hepatitis C virus (HCV) according to the method of the present invention and electron micrographs of the protein particles.
Figure 9:
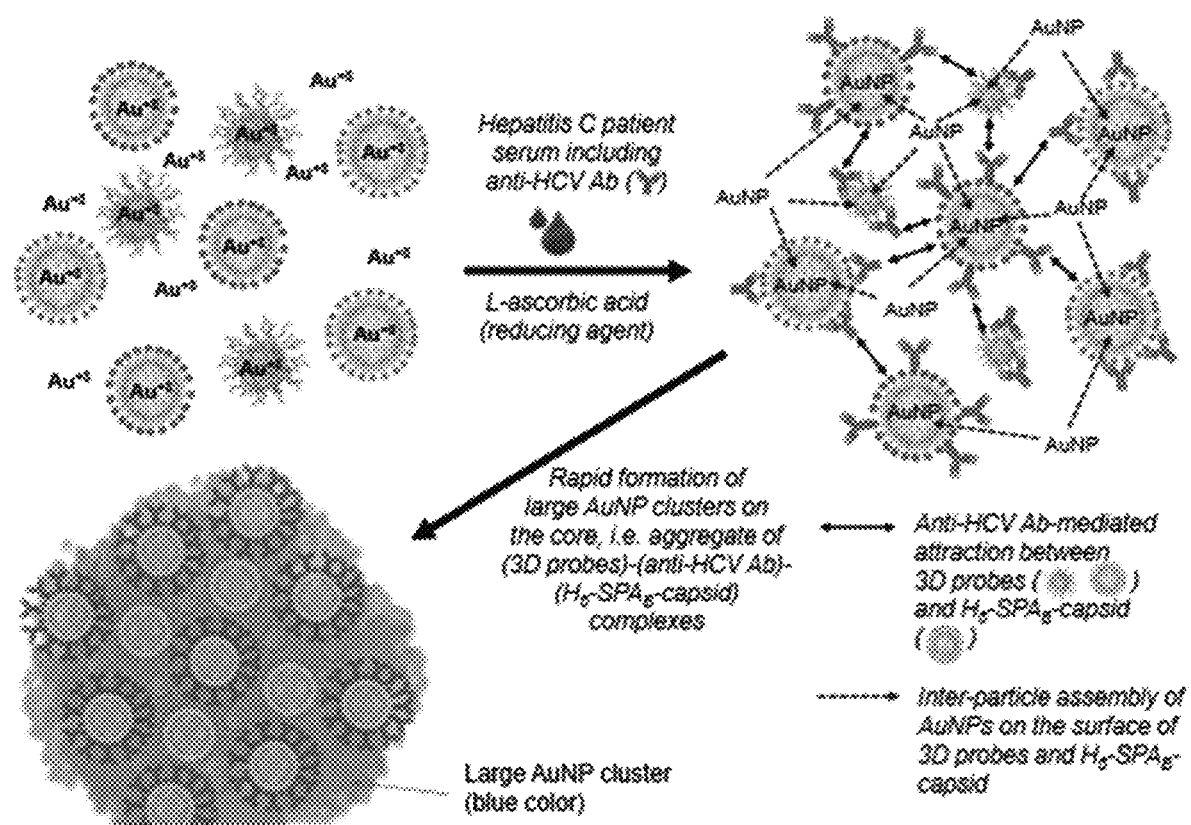
FIG. 9 illustrates a schematic diagram illustrating a principle of detecting an HCV antibody present in a blood sample of a patient with hepatitis C according to the method of the present invention.

That is, in another embodiment of the present invention, a method according to the present invention was used to detect a hepatitis C virus (HCV)-specific antibody from a patient with hepatitis C. First, 1) an expression vector with a $H_6$-SPAB-HBVC capsid structure, 2) an expression vector with a $H_6$-c33c(HCV epitope)-HBVC capsid structure and 3) an expression vector with a hFTN(human ferritin)-511p-c100p-c22p(HCV epitope)-H6 structure were respectively expressed in Escherichia coli to prepare three types of protein particles (FIG. 8). It was expected that protein particles prepared from the vector (1) include hexa-histidine and SPAB exposed from surfaces thereof, thereby biding with Au ions and an Fc domain of an antibody, and the vectors (2) and (3) include hepatitis C-specific epitopes exposed from surfaces thereof and thus bind with HCV-specific antibodies in a patient sample (FIG. 9).

Figure 10:
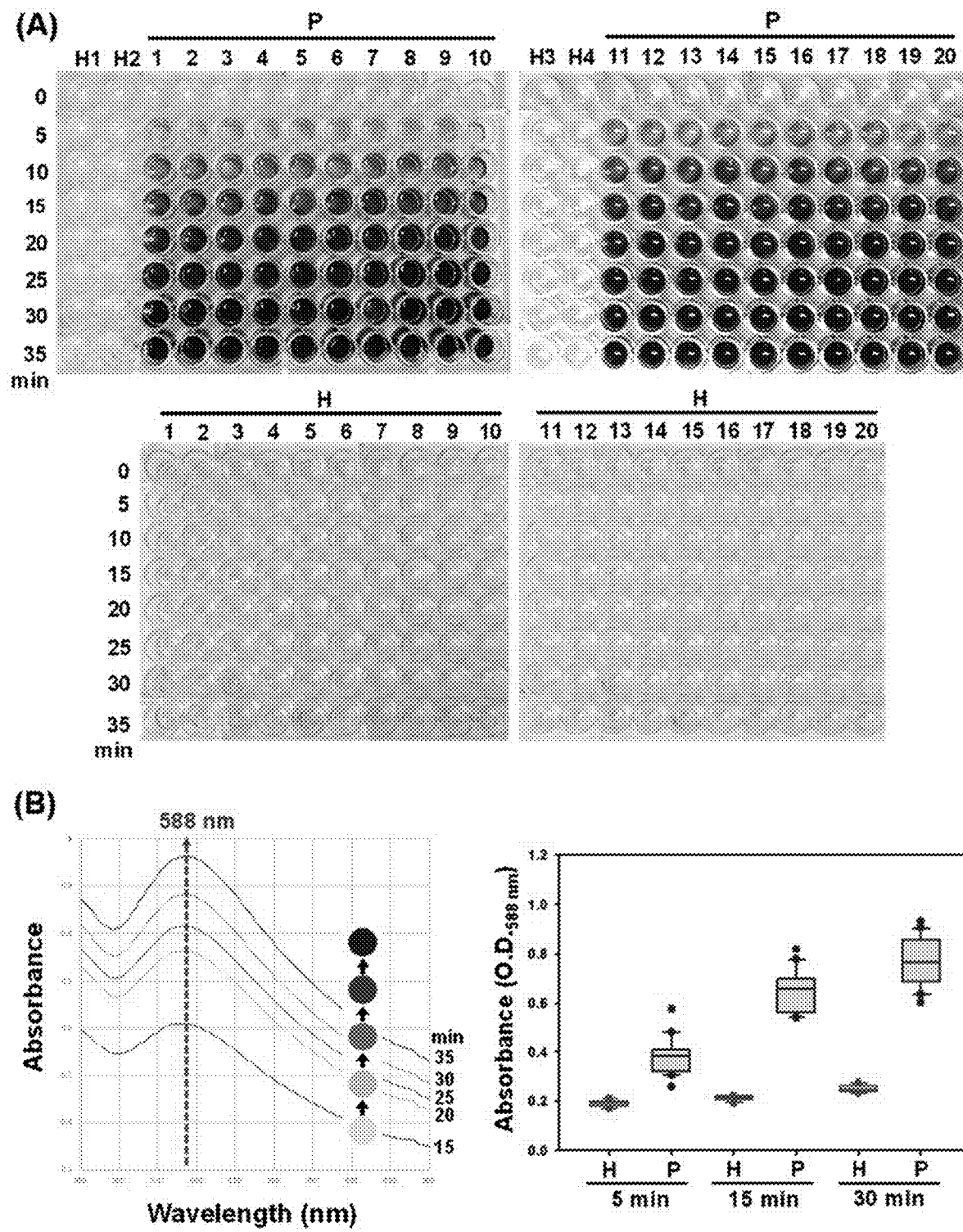
FIG. 10(A) illustrates test results of blood samples of a patient with hepatitis C and a normal individual according to the method of the present invention.
FIG. 10(B) illustrates absorbances dependent upon antigen-antibody complex sizes in a patient with hepatitis C and absorbance changes dependent upon time. Particularly, it is illustrated that an absorbance increases at a specific wavelength of 588 nm over time, and clusters are formed in the shape shown in the TEM image. In addition, a box plot illustrates a difference in absorbances at each time of a normal individual group and a patient group.
Figure 11:
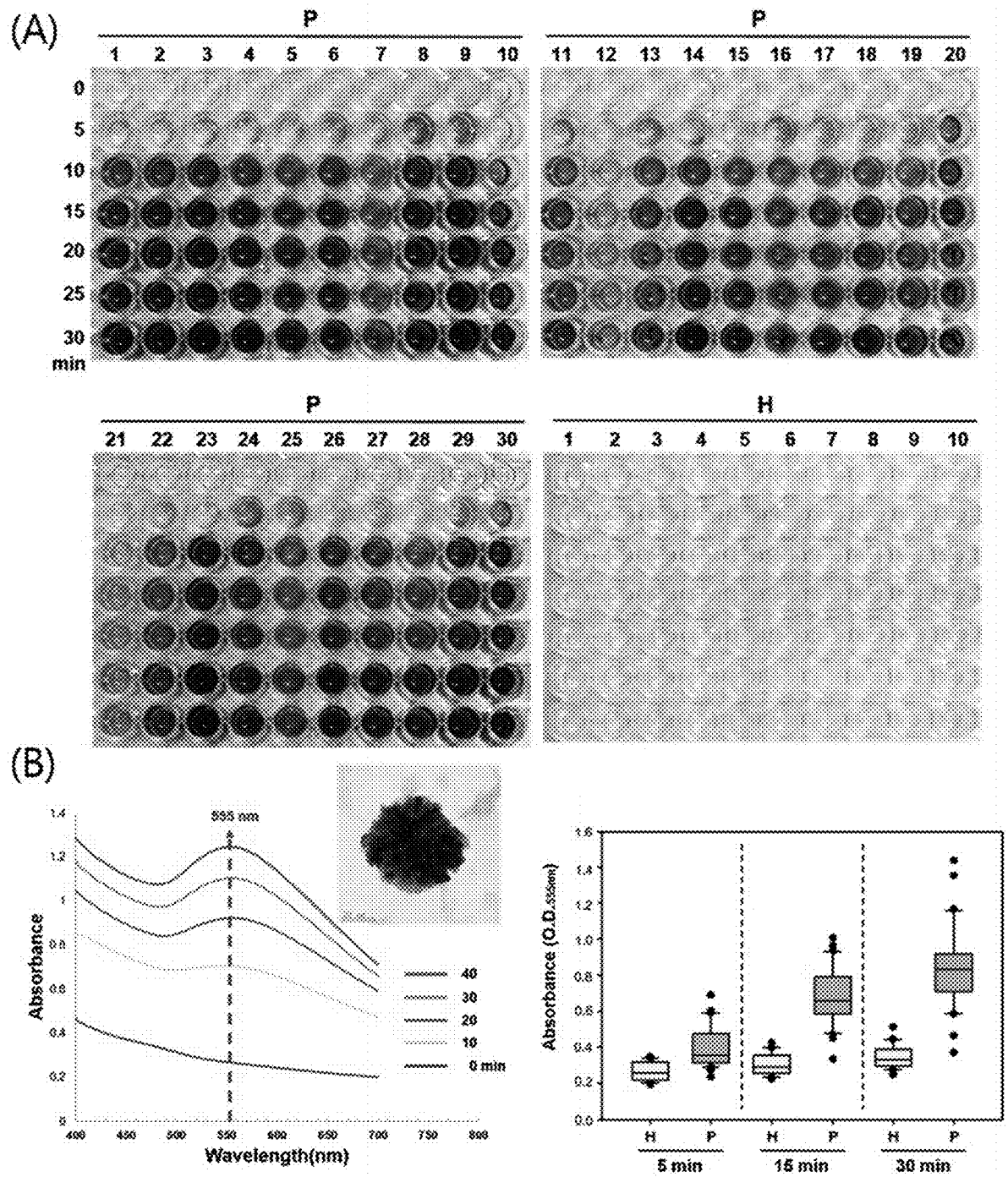
FIG. 11(A) illustrates test results of blood samples of a patient with HIV and a normal individual according to the method of the present invention.
FIG. 11(B) illustrates absorbances dependent upon antigen-antibody complex sizes and absorbance changes dependent upon time in a patient with HIV. Particularly, it is illustrated that absorbance increases at a specific wavelength of 588 nm over time, and clusters are formed in the shape shown in the TEM image. In addition, a box plot illustrates a difference in absorbances at each time of a normal individual group and a patient group.

It was confirmed that, when Au ions were adsorbed into an aqueous solution mixed with protein particles, and then a blood sample of a patient and a blood sample of a normal individual were respectively injected thereinto, clusters of protein particles and Au particles were formed and, thus, a blue chromogenic reaction occurred only in the patient blood sample (FIGS. 10 and 11).

Accordingly, in another aspect of the present invention, the present invention relates to a method of detecting an antiviral antibody using self-amplification of a detection signal, the method including (a) a step of simultaneously inducing an antigen-antibody immune response and an Au particle formation reaction by reduction of Au ions in an assay solution prepared by, to a pre-assay solution in which all of an antigen for detecting an antiviral antibody, free Au ions, and adsorbed Au ions are present, adding a sample, which contains an antiviral antibody binding specifically to the antigen, and a reducing agent; and (b) a step of confirming the presence or absence of a virus by a chromogenic reaction through the Au particle formation.

In the present invention, the term "antigen for virus detection" may be any virus protein specifically binding to an antibody capable of detecting a virus and may include, as well as a virus protein, any types of amino acids, such as virus peptides or epitopes, translated from virus genes.

In the present invention, the term "epitope" refers to a specific site binding to an antibody on an antigen molecule; or a conjugate of a T cell receptor (TCR) and a major tissue complex (MHC) and may be referred to as an antigenic determinant.

For example, hepatitis C virus (HCV) belongs to the Flaviviridae family causing non-A and non-B hepatitis. The HCV genome, which includes single-stranded RNA, expresses a polyprotein composed of about 3,010 amino acids (Choo et al., Science, 244:359-362, 1989). Polyprotein expressed by HCV is cut by host cell proteases and virus proteases into 10 functionally different proteins.

The HCV gene is composed of NH2-C-E1-E2-p7-NS2-NS3-NS4A-NS4B-NS5A-NS5B-COOH (Steven Rosenberg, J. Mol. Biol., 313:451-464, 2001). This protein is greatly classified into structural proteins including C (core), E1, E2 and p7; and non-structural proteins including NS2, NS3, NS4A, NS4B, NS5A, and NS5B.

C (core) protein of HCV is believed to be responsible for encapsidation of HCV genomic RNA and to play an important role in the development of hepatoma by regulating gene transcription, growth and proliferation of host cells. E1 and E2 are type-1 transmembrane proteins and virus envelope proteins, known to play important roles in cell infection. $E_1$ protein had not attracted great attention in the past because it does not induce neutralizing antibodies. Recently, however, E1 protein was developed as a therapeutic vaccine by Innogenetics, Co. in Belgium, which is in the process of phase II clinical trial following successful phase I clinical trial with chimpanzees. It is encouraging that E1 protein can be effectively used for the treatment of 1b type HCV infection that has not been successfully treated by alpha-interferon.

E2 protein, which is a major envelope protein of a virus, has been known as a multi-functional protein which, in addition to structural roles, conjugates with the assumed cell receptor CD81, and it nullifies both the immune system of a host cell and interferon-mediated antiviral reaction, which leads to oncogenesis or autoimmune liver disease. Accordingly, E2 is recognized as a major antigen for the development of an HCV vaccine and a major target for the development of an anti-HCV drug. The function of P7 protein has not been known. NS2 protein is a part of a metallo-protease, and NS3 harbors serine protease of HCV at its N-terminus and RNA helicase domain of its C-terminus.

NS4A is a cofactor of viral protease, and NS4B has been found to have a potential for tumorigenesis. NS5A was reported to function to endow HCV resistance against interferon and antiapoptosis. NS5B is known to act as a viral RNA-dependent RNA polymerase. It will be apparent to those skilled in the art that epitopes of such HCV constituent proteins may be used as a virus specific epitope of the present invention.

In the present invention, an antigen for detecting an antiviral (HCV) antibody present in the pre-assay solution may be selected from the group consisting of c22p, c33c, 5-1-1p, c100p, and a fused epitope of two or more thereof. The fused epitope may be selected from the group consisting of c22p-c33c, c22p-5-1-1p, c22p-c100p, c33c-5-5-1p, c33c-c100p, 5-1-1p-c100p and c22p-5-1-1p-c100p, but the present invention is not limited thereto.

The term "virus" used in the present invention refers to an obligatory intracellular parasite that has DNA or RNA as a nucleic acid, starts proliferation from the nucleic acid, does not proliferate through binary fission, and does not have an enzyme system required for ATP production.

The virus of the present invention includes a naked virus and an enveloped virus. Particularly, a virus according to an embodiment of the present invention may be an enveloped virus.

In the present invention, the enveloped virus may include, particularly, DNA viruses such as herpesvirus, poxvirus and hepadnavirus, and RNA viruses such as flavivirus, togavirus, coronavirus, hepatitis D, orthomyxovirus, paramyxovirus, rhabdovirus, bunyavirus, filovirus, human immunodeficiency virus (HIV), and retrovirus.

The orthomyxovirus includes influenza virus A, influenza virus B, influenza virus C, isavirus, thogotovirus and quaranjavirus genera.

The coronavirus includes alpha coronavirus, beta coronavirus, gamma coronavirus and delta coronavirus genera.

The paramyxovirus encompasses paramyxovirus, rubella virus, morbillivirus and pneumovirus genera.

The human immunodeficiency virus (HIV) genome consists of two positive single-stranded RNAs that encode nine viral gene factors. RNA is surrounded by a conical capsid consisting of about 2,000 virus proteins p24. The virus contains single-stranded RNA, nuclear capsid protein p7, and enzymes necessary for the formation of virion proteins (reverse transcriptase, proteinase, ribonuclease, integrase).

A substrate composed of a virus protein p17 surrounds the capsid again to preserve virions. The substrate is again surrounded by a viral membrane composed of phospholipid bilayers. The viral membrane is first formed when a new virus emerges from a host cell. The viral membrane being created is buried in a cell membrane of a host cell and consists of about 70 complex HIV proteins that protrude from a host cell's protein and a virus particle surface.

The complex HIV protein, known as Env, consists of a hat consisting of three glycoprotein120 molecules; and a stem, which anchors a protein structure to a viral membrane, consisting of three gp41 molecules. Glycoprotein conjugates are important at the start of an infection cycle, enabling a virus to attach and fuse to target cells. Two surface glycoproteins of a virus, particularly gp120, are known as subjects for future therapeutic agent and vaccine development.

Two TAT proteins (p16 and p14) are transcriptional transactivators for the LTR promoter acting by binding to the TAR RNA element. The TAR may also be processed into microRNAs that regulate the apoptosis genes ERCC1 and IER3. The Rev protein (p19) is involved in shuttling RNAs from the nucleus and the cytoplasm by binding to the RRE RNA element. The Vif protein (p23) prevents the action of APOBEC3G (a cellular protein that remove amines from DNA and RNA hybrids or interferes with Pol proteins). The Vpr protein (p14) arrests a host at G2/M and prevents cellular division thereof. The Nef protein (p27) down-regulates the MHC class I and class II molecules as well as CD4 (a major viral receptor) of T cells.

Nef also interacts with SH3 domains. The Vpu protein (p16) influences the release of new virus particles from infected cells. GAG gene expresses matrix proteins (MA, GAG p17), capsid proteins (CA, GAG p24), nucleic acid capsids (NC, GAG p'7), etc., which are cores of viral particles. Pol gene contains an enzyme gene related to viral proliferation and is composed of an RT portion involved in reverse transcriptase expression of viral RNA, a PR responsible for protease, an integrase-related IN, etc.

In addition, TAT gene is known to express a regulator that activates the proliferation of a virus during an infection process, and, on the other hand, Nef gene is known to play a role in inhibiting the proliferation of a virus along with the LTR portion. The Long Term Repeat (LTR), in which the same nucleotide sequences are repeated, is attached to both ends of the entire HIV RNA. LTR sites act as switches that regulate the production of a new virus or can be triggered by proteins of HIV or host cells. The retroviral Psi element is involved in viral genome packaging and is recognized by gag and rev proteins. The SLIP element (TTTTTT) is known to be involved in the frameshift in the gag-pol reading frame required to make functional Pol. It will be apparent to those skilled in the art that an epitope of HIV can be used for the virus detection of the present invention.

In the present invention, the antigen for detecting an antiviral (HIV) antibody present in the pre-assay solution may be selected from the group consisting of gp41, p24 and gp100, but the present invention is not limited thereto.

DNA of the human papilloma virus (HPV) contains 8000 base pairs and is surrounded by a pentagonal capsid protein of the pentagon, not a lipid membrane. The capsid protein consists of two structural proteins, L1 and L2, which are expressed later in a viral replication cycle. In the genome of all human papillomavirus (HPV), there are eight ORFs, and each ORF is divided into three functional sites. The functional sites consist of E1-E7 gene necessary for virus replication, L1-L2 gene expressing structural proteins constituting virions, and LCR gene regulating the replication and transcription of a virus.

E6 binds to p53 and promotes ubiquitination of p53, thereby inhibiting the function of p53 as a cancer tumor suppressor gene. It also induces the degradation of BAK, a pro-apoptotic protein. The activation of telomerase activates the cell cycle of host cells, and E7 interacts with retinoblastoma (RB) to degrade RB. Through this, E2F, a transcription promoter that has been inhibited by RB, is released. In addition, the cell cycle of the host cell is activated by the activation of cyclin E and cyclin A acting on the cell cycle S phase, and, when infected with the human papillomavirus through the activation of these genes, cervical cancer may be developed. However, the roles of other genes such as E1, E2, and E4 in HPV in cancer development processes, is still unknown.

L1 self-assembles to form pentameric pensommers. These capsomers form capsids through disulfide bonds with adjacent L1 molecules to package human papilloma virus DNA, and L2 is present in lesser amounts than L1, facilitating the packaging of the viral genome. In addition, human papillomaviruses are known to play an important role when penetrating new host cells.

Accordingly, in the present invention, the antigen for detecting an antiviral (HIV) antibody present in the pre-assay solution may be L1 or L2, but the present invention is not limited thereto.

Middle East Respiratory Syndrome Coronavirus (MERS-CoV), a type of coronavirus, was detected in samples collected from the lungs of a 60-year-old male with acute pneumonia and acute renal failure in Jidda, Saudi Arabia. MERS-CoV is a plus-sense, single stranded novel RNA beta coronavirus that is known to cause Middle East Respiratory Syndrome.

Accordingly, in the present invention, an antigen for detecting an antiviral (MERS-CoV) antibody present in the pre-assay solution may be a MERS-CoV surface protein, but the present invention is not limited thereto.

Hepatitis A virus (HAV) is classified into the genus Picornaviridae and the genus *Hepatovirus,* has no encapsulation, is a regular icosahedron, and has a particle size of 27 to 32 nm. The virion consists of three major structural polypeptides (VP1, VP2 and VP3).

Accordingly, in the present invention, an antigen for detecting an antiviral (HAV) antibody present in the pre-assay solution may be VP1, VP2, VP3 or an epitope prepared by extracting or connecting portions thereof, but the present invention is not limited thereto.

In the present invention, the adsorbed Au ions may be any one adsorbed to a material capable of adsorbing Au ions, preferably a material capable of being adsorbed to amino acids, more preferably a material capable of being adsorbed to an amino acid selected from the group consisting of histidine, lysine and arginine, but the present invention is not limited thereto.

In the present invention, the reducing agent may be any material capable of reducing Au ions into Au particles under reaction conditions of the present invention, preferably may be selected from the group consisting of ascorbic acid, imidazole, pyrazole, histamine, hydroxyl amine, citric acid, and sodium borohydride.

In the present invention, the sample may be selected from the group consisting of blood, plasma, serum, urine, saliva, oral mucosa, and saliva, but the present invention is not limited thereto.

In the present invention, the concentration of the Au ions (free Au ions +adsorbed Au ions) present in the pre-assay solution may be 1 mM to 10 mM, but the present invention is not limited thereto.

In the present invention, the concentration of the reducing agent present in the assay solution may be 0.005 M to 0.1 M, but the present invention is not limited thereto.

In the present invention, the amount of the sample may be 10 µl to 30 µl, but the present invention is not limited thereto.

In the present invention, when the concentration of the Au ions, the concentration of the reducing agent, and the amount of the sample are smaller than reference values, effect disease marker detection may not be performed. When the concentration of the Au ions, the concentration of the reducing agent, and the amount of the sample are greater than reference values, negative effects such as false positive effect may be exhibited.

In the present invention, the antigen for virus detection may be exposed form surfaces of protein particles. From the surfaces of the protein particles, a tag selected from the group consisting of histidine, lysine, and arginine capable of adsorbing Au ions may be further exposed.

In the present invention, an immune response of the antigen for virus detection may occur on surfaces of protein particles. The tag may adsorb Au ions to induce aggregation of Au particles in the presence of a reducing agent.

In the present invention, the protein particles may be any particles formed by a self-assembly function of a protein, preferably may be selected from the group consisting of ferritin, ferritin-like proteins, magnetosome-constituting proteins, virus-constituting proteins (e.g. hepatitis B virus core protein, tobacco mosaic virus) DNA binding proteins (DPS), and proteosome, but the present invention is not limited thereto. In the present invention, the virus-constituting proteins may be selected from the group consisting of capsid proteins of human hepatitis B virus.

In the present invention, the sizes of the protein particles may be 10 nm to 50 nm, but the present invention is not limited thereto.

In the present invention, by self-amplification of a detection signal, a small amount of antiviral antibody is detected and a resultant result is expressed by a color change that can be observed by the naked eye. Such self-amplification of a signal is caused by a phenomenon that Au ions dissolved in a solution for diagnosis are reduced into Au particles by a reducing agent. As the sizes of Au particles increase, a resultant color change is expressed as a signal that can be confirmed by the naked eye.

In the case of protein particles used in the present invention, hexa-histidine is fused to and expressed in monomers thereof. Here, since histidine amino acids have a property of binding with Au ions, Au ions bound to aggregates generated due to an antigen-antibody reaction react with a reducing agent, thereby being reduced into Au particles. The sizes of the Au particles increase as other Au ions are reduced, thereby forming larger Au particles. Such resultant aggregates are colored.

In the case of a normal individual serum, an antigen-antibody reaction does not occur. Accordingly, a generation speed of aggregates due to Au particles is low, whereby a time taken until a color is expressed is significantly slow. Through such a color change, a virus-bearing patient may be distinguished from a normal individual.

In the present invention, an antiviral antibody contained in a sample is exposed form surfaces of protein particles, thereby binding to a domain capable of binding to an Fc domain of the antibody.

In the present invention, a domain capable of binding to the Fc domain of the antibody may be selected from the group consisting of B domain of Staphylococcal protein A and protein G, but the present invention is not limited thereto.

In the present invention, a domain capable of binding to the Fc domain of the antibody may be bound to a linker protein exposed from surfaces of the protein particles.

In the present invention, the linker protein is not specifically limited so long as it is an amino acid capable of effectively exposing a domain, capable of binding to the Fc domain of the antibody, from surfaces of protein particles, and, preferably, may have an amino acid sequence such as G4SG4T or G4SG4.

In the present invention, the chromogenic reaction may more rapidly occur in a group, to which a sample of a patient is added, than a group to which a normal sample is added. In the patient group, the chromogenic reaction occurs within a minimum of 5 minutes to a maximum of 10 minutes. However, a reaction time may be changed according to reaction conditions.

In the present invention, the chromogenic reaction may be detected using any method of detecting changes in visible light and, preferably, may be detected by the naked eye or using a spectrophotometer, and an absorbance may be detected at 500 to 600 nm, but the present invention is not limited thereto.

Another aspect of the present invention relates to a method of providing information for disease diagnosis using self-amplification of a detection signal, the method including (a) a step of simultaneously inducing an antigen-antibody immune response and an Au particle formation reaction by reduction of Au ions in an assay solution prepared by, to a pre-assay solution in which all of an antibody or antigen for detection of a disease-specific marker, free Au ions, and adsorbed Au ions are present, adding a sample, which contains a disease-specific antigen or antibody binding specifically to the antibody or the antigen, and a reducing agent; and (b) a step of confirming the presence or absence of a disease-specific marker by a chromogenic reaction through the Au particle formation.

The present invention also relates to a disease diagnosis method using self-amplification of a detection signal, the method including (a) a step of simultaneously inducing an antigen-antibody immune response and an Au particle formation reaction by reduction of Au ions in an assay solution prepared by, to a pre-assay solution in which all of an antibody or antigen for detection of a disease-specific marker, free Au ions, and adsorbed Au ions are present, adding a sample, which contains a disease-specific antigen or antibody binding specifically to the antibody or the antigen, and a reducing agent; and (b) a step of confirming the presence or absence of a disease-specific marker by a chromogenic reaction through the Au particle formation.

In an embodiment of the present invention, an antibody binding specifically to Troponin I (TnI) was exposed to the protein particles of the present invention in a blood sample of a patient with acute myocardial infarction and a blood sample of a normal individual, and it was confirmed that a chromogenic reaction rapidly occurred in the patient blood sample (FIG. 2). That is, it is obvious to those of ordinary skill in the art that, when a disease-specific marker is detected according to the present invention, the disease may be diagnosed.

Accordingly, in the present invention, the disease may be acute myocardial infarction, but the present invention is not limited thereto.

In the present invention, when the disease is acute myocardial infarction, the disease-specific antibody may be an antibody specifically binding to troponin I, but the present invention is not limited thereto.

In the present invention, the disease may be hepatitis C, acquired immune deficiency syndrome (AIDS), or hepatitis A, but the present invention is not limited thereto.

In the present invention, when the disease is hepatitis C, the disease-specific antibody may be an antibody specifically binding to HCV and, when an antigen is exposed from surfaces of protein particles, may be selected from the group consisting of c22p, c33c, 5-1-1p, and c 100p of HCV and a fused epitope of two or more thereof. The fused epitope may be selected from the group consisting of c22p-c33c, c22p-5-1-1p, c22p-c100p, c33c-5-5-1p, c33c-c100p, 5-1-1p-c100p and c22p-5-1-1p-c100p, but the present invention is not limited thereto.

In the present invention, when the disease is AIDS, the disease-specific antibody may be an antibody binding specifically to HIV and, when an antigen is exposed from surfaces of protein particles, may be selected from the group consisting of gp41, p24 and gp100 of HIV, but the present invention is not limited thereto.

In the present invention, when the disease is hepatitis A, the disease-specific antibody may be an antibody specifically binding to HAV and, when an antigen is exposed from surfaces of protein particles, may be one or more epitopes selected from the group consisting of VP1, VP2, VP3 or an epitope prepared by extracting or connecting portions thereof, but the present invention is not limited thereto.

In the present invention, the disease may be cancer. The cancer may be may be selected from the group consisting of lung cancer, bronchial cancer, colorectal cancer, prostate cancer, breast cancer, pancreatic cancer, stomach cancer, ovarian cancer, bladder cancer, brain cancer, thyroid cancer, esophageal cancer, uterine cancer, liver cancer, kidney cancer, biliary cancer, glial cancer blastoma, and testicular cancer.

In the present invention, when the disease is cancer, the disease-specific antibody may be an antibody specifically binding to a tumor marker, but the present invention is not limited thereto.

In the present invention, the tumor marker may be as shown in Table 1 below for each cancer type, but the present invention is not limited thereto.

TABLE 1

Tumor marker for each carcinoma

| Carcinoma | Tumor markers |
| --- | --- |
| Brain, hard tumor | SCC |
| Lung cancer | SLX, NSE, SCO, ADH, ACTH |
| Liver cancer | AFP, PIVKA-II, ALP |
| Gastroduodenal cancer | CA19-9, CEA, AFP |
| Prostate cancer | PSA, PA |
| Teaticular cancer | AFP, HCO, NSE |
| Thyroid cancer | CEA, Calcitonin, Thyroglobulin |
| Breast cancer | CA 15-3, CEA, CA549, TPA |
| pancreatic cancer | CA19-9, Elatase I, CA50, Du-Pan-2, SPAN-1, KMO1, POA, PST |
| Colon cancer | CEA, NCC-ST-439 |
| Uterine cancer | SCC, CEA, hCG |
| Ovarian cancer | CA125, CA72-4 |
| Blood cancer | β-2-Microglobulin |

In the present invention, when the disease is lymphoma or leukemia, the disease-specific antibody may be an antibody that specifically binds to CD20, CD30, CD33 or CD52, but the present invention is not limited thereto.

In the present invention, when the disease is breast cancer, colon cancer, lung cancer, or ovarian cancer, the disease-specific antibody may be an antibody specifically binding to EGFR, ERBB2, ERBB3, MET, IGF1R, EPHA3, TRAILR1, TRAILR2, FAP, Tenascin, EpCAM, CEA, gpA33, Mucin, TAG-72, CAIX, PSMA or a Folate-binding protein, but the present invention is not limited thereto.

In the present invention, the disease may be an infectious disease. The infectious disease may be selected from the group consisting of flu (influenza), smallpox, polio, foot and mouth disease, Ebola, measles, yellow fever, dengue fever, SARS, pneumonia, tuberculosis, cholera, typhoid, dysentery, diphtheria and Lyme disease, but the present invention is not limited thereto.

In the present invention, when the disease is influenza, the disease-specific antibody may be an antibody binding specifically to influenza virus, but the present invention is not limited thereto.

Influenza virus is a single stranded RNA virus belonging to Orthomyxoviridae, has two glycoprotein surface antigens, i.e., hemagglutinin and neuraminidase, and is classified into influenza A, B and C according to antigenicity. Type A and B mainly cause epidemic outbreaks, type A is classified as a subtype according to the characteristics of HA (H1-H15) and NA (N1-N9), type B has no subtype. Accordingly, when the flu is diagnosed by the method of the present invention, the antibody used in the present invention may be an antibody specific to each influenza virus subtype, but the present invention is not limited thereto.

In the present invention, when the disease is polio, the disease-specific antibody may be an antibody specifically binding to a poliovirus, but the present invention is not limited thereto.

In the present invention, when the disease is Ebola, the disease-specific antibody may be an antibody specifically binding to an Ebola virus, but the present invention is not limited thereto. When the disease is measles, the disease-specific antibody may be an antibody specifically binding to a measles virus that is a type of paramyxovirus, but the present invention is not limited thereto. When the disease is yellow fever, the disease-specific antibody an antibody specifically binding to a yellow fever virus that belongs to the family Flavivirus, but the present invention is not limited thereto. When the disease is dengue fever, the disease-specific antibody may be an antibody specifically binding to a dengue virus, but the present invention is not limited thereto.

In the present invention, the disease may be an autoimmune disease. The autoimmune disease may be selected from the group consisting of rheumatoid arthritis, type 1 diabetes, Crohn's disease, ulcerative colitis, Behcet's disease, lupus, scleroderma, psoriasis and vitiligo, but the present invention is not limited thereto.

In the present invention, when the disease is Sjogren's syndrome, the disease-specific antibody may be an anti-Ro (Sjogren's syndrome A, SSA) antibody or an anti-La (Sjogren's syndrome B, SSB) antibody, but the present invention is not limited thereto.

In the present invention, when the disease is multiple sclerosis, the disease-specific antibody may be an anti-MOG antibody, an anti-myelin antibody or an anti-KIR4.1 antibody, but the present invention is not limited thereto.

In the present invention, when the disease is stroke, the disease-specific antibody may be an anti-NR2A/2B and metalloproteinase (MMP) antibody, an antinuclear antibody (ANA), an antiphospholipid antibody (APL), an anti-D-dimer antibody, an anti-S1000 antibody, an anti-B-type natriuretic peptide (BNP) antibody, or an anticardiolipin antibody (ACL), but the present invention is not limited thereto.

In the present invention, when the disease is cerebral hemorrhage, the disease-specific antibody may be anti-glial fibrillary acidic protein (GFAP) antibody, anti-asymmetric dimethylarginine (ADMA) antibody, or anti-D-dimer antibody, but the present invention is not limited thereto.

The present invention also relates to a disease diagnosis kit using self-amplification of a detection signal.

In the present invention, the kit may include a pre-assay solution containing an antigen or antibody for detecting a disease-specific marker, free Au ions, and adsorbed Au ions; and a reducing agent. Here, it is preferred to store the pre-assay solution and the reducing agent in different containers.

In the present invention, the kit may include an external package. The external package may include instructions for use of components thereof.

EXAMPLES

Hereinafter, the present invention will be described in more detail with reference to the following Examples. It will be apparent to those skilled in the art that the Examples are merely for concretely explaining the invention and therefore, there is no intent to limit the invention to the Examples.

Example 1

Preparation of Expression Vectors for Synthesis of hFTN and HBV Capsid Protein Particles Expression vectors for manufacturing protein particles, $H_6$-SPAB-capsid, $H_6$-c33c-capsid, $H_6$-gp41-capsid, $H_6$-p24-capsid, hFTN-511p-c100p-c22p-H6, hFTN-epl-H6, hFTN-ep2-H6, and hFTN-ep3-H6, were prepared according to schematic vector diagrams summarized in Table 1.

All of the prepared plasmid expression vectors were subjected to agarose gel-purification, and then total DNA sequences of each thereof were confirmed.

In particular, a PCR product required to prepare each of the expression vectors was produced using a primer set shown in Table 2, and then the resultant PCR product was sequentially inserted into a pT7-vector, thereby constituting an expression vector for expressing each protein particle type.

Vectors for expressing each of the protein particle type are as follows: pT7-$H_6$-SPAB-capsid, pT7-$H_6$-c33c-capsid, pT7-$H_6$-gp41-capsid, pT7-$H_6$-p24-capsid, pT7-hFTN-511p-c100p-c22p-H6, pT7-hFTN-epl-H6 pT7-hFTN-ep2-H6 and pT7-hFTN-ep3-H6.

TABLE 2

Expression vector constructions for manufacturing protein particles

| Protein particles | Expression vectors |
|---|---|
| $H_6$-SPA$_B$-capsid | $NH_2$-NdeI-$H_6$-HBVC-(SPA$_B$)$_2$-HBVC-ClaI-COOH |
| $H_6$-c33c-capsid | $NH_2$-NdeI-$H_6$-HBVC-c33c-HBVC-ClaI-COOH |
| $H_6$-gp41-capsid | $NH_2$-NdeI-$H_6$-HBVC-gp41-HBVC-ClaI-COOH |
| $H_6$-p24-capsid | $NH_2$-NdeI-$H_6$-HBVC-p24-HBVC-ClaI-COOH |
| hFTN-511p-c100p-c22p-$H_6$ | $NH_2$-NdeI-hFTN-XhoI-linker(G3SG3TG3SG3)-511p-c100p-c22p-$H_6$-HindIII-COOH |
| hFTN-ep1-$H_6$ | $NH_2$-NdeI-hFTN-XhoI-linker(G3SG3TG3SG3)-ep1-$H_6$-HindIII-COOH |
| hFTN-ep2-$H_6$ | $NH_2$-NdeI-hFTN-XhoI-linker(G3SG3TG3SG3)-ep2-$H_6$-HindIII-COOH |
| hFTN-ep3-$H_6$ | $NH_2$-NdeI-hFTN-XhoI-linker(G3SG3TG3SG3)-ep3-$H_6$-HindIII-COOH |

TABLE 3

Primer sets for PCR to manufacture expression vectors

| Protein particles | Primers |
|---|---|
| $H_6$-SPA$_8$-capsid | 5' primer: CTC GAG GCA CCG AAA GCT GAT AAC<br>3' primer: GGA TCC GTC AGC TTT TAG TGC TTG |
| $H_6$-c33c-capsid | 5' primer: CTC GAG GCG GTG GAC TTT ATC CCT<br>3' primer: GGA TCC ACA CGT ATT GCA GTC TAT |
| $H_6$-gp41-capsid | 5' primer: CTC GAG ATC CTG GCT GTG GAA CGC<br>3' primer: GGA TCC GAT CAA CTT TCC ACT AGC |
| $H_6$-p24-capsid | 5' primer: CTC GAG CCG GAA GTA ATC CCG ATG<br>3' primer: GGA TCC TCC CAC TCC CTG ACA TGC |

Example 2

Biosynthesis and Separation Purification of hFTN and HBV Capsid Protein Particles 2-1. Biosynthesis of Protein Particles

*E. coli* strain BL21(DE3)[F-ompThsdSB (rB-mB-)] was transformed with each of the expression vectors manufactured according to Example 1, and ampicillin-resistant transformants were selected. The transformed E. coli were cultured in a flask (250 mL Erlenmeyer flask, 37° C., 150 rpm) containing 50 mL of a Luria-Bertani (LB) medium (containing 100 mg of $L^{-1}$ ampicillin).

When the turbidity (O.D 600) of the medium reached about 0.4 to 0.6, IPTG (Isopropyl-β-D-thiogalactopyranosid) (1.0 mM) was injected thereinto to induce expression of the recombinant gene. After culturing at 20° C. for 12 to 16 hours, the cultured *Escherichia coli* was centrifuged at 4,500 rpm for 10 minutes to obtain a cell precipitate. The obtained cell precipitate was suspended in 5 ml of a lysis solution (10 mM Tris-HCl buffer, pH 7.5, 10 mM EDTA), and lysed using an ultrasonic crusher (Branson Ultrasonics Corp., Danbury, Conn., USA), followed by centrifuging at 13,000 rpm for 10 minutes, followed by separating a supernatant from an insoluble aggregate. The separated supernatant was purified.

2-2. Purification of Protein Particles

To purify the fused protein particles, recombined by self-assembly, expressed in Example 2-1, the following three-step purification process was performed. First, 1) $Ni^{2+}$-NTA affinity chromatography using a combination between histidine fused to the recombined protein and nickel was performed, and then 2) the recombined protein was concentrated and a buffer of the concentrated protein was exchanged such that self-assembly of monomers occurred, and 3) sucrose gradient ultracentrifugation was performed to isolate only the self-assembled protein particles. A detailed description of each step follows.

1) $Ni^{2+}$-NTA Affinity Chromatography

To purify each of the recombined proteins, *Escherichia coli* cultured according to the aforementioned method was collected, and a cell pellet was resuspended in 5 mL of a lysis solution (pH 8.0, 50 mM sodium phosphate,300 mM NaCl, 20 mM imidazole), followed by crushing the cells using an ultrasonic crusher. The crushed cell solution was centrifuged at 13,000 rpm for 10 minutes to isolate only a supernatant. Next, the recombined protein was separated using a $Ni^{2+}$-NTA column (Qiagen, Hilden, Germany) (washing buffer: pH 8.0, 50 mM sodium phosphate, 300 mM NaCl, 50 mM imidazole/elution buffer: pH 8.0, 50 mM sodium phosphate, 300 mM NaCl, 100 mM imidazole).

2) Concentration and Buffer Exchange 3 ml of the recombined protein eluted through $Ni^{2+}$-NTA affinity chromatography was contained in an ultracentrifugal filter (Amicon Ultra 10K, Millipore, Billerica, Mass.), followed by centrifuging at 5,000 rpm until 1 ml of a solution remained on the column. The buffer of the protein particles was exchanged with a Tris-HCl (50 mM Tris-HCl, 500 mM NaCl, pH 7.0) buffer (in the case of hFTN particles, PBS buffer (2.7 mM KCl, 137 mM NaCl, 2 mM $KH_2PO_4$, 10 mM $Na_2HPO_4$, pH 7.4)) so that self-assembly of monomers occurred.

3) Sucrose-Gradient High-Speed Centrifugation

To a Tris-HCl (50 mM Tris-HCl, 500 mM NaCl, pH 7.0) buffer (in the case of hFTN particles, a PBS buffer (2.7 mM KCl, 137 mM NaCl, 2 mM $KH_2PO_4$, 10 mM Na2HPO4, pH 7.4)), sucrose was added to each concentration, thereby preparing a solution including sucrose at a concentration of each of 60%, 50%, 40%, 30%, and 20%. Next, 2 ml of a sucrose solution at each concentration (60 to 20%) was added to a high-speed centrifuge tube (ultraclear 13.2 ml tube, Beckman) in a high-concentration order. After containing a solution, 1 ml of a recombined protein solution was finally added, followed by performing high-speed centrifugation at 24,000 rpm and 4° C. for 16 hours (Ultracentrifuge L-90k, Beckman). After centrifugation, 40 to 50% of the sucrose solution was carefully removed, and the buffer of the recombined protein was replaced with a new buffer using an ultracentrifugal filter and a Tris-HCl buffer as described in step 2).

Example 3

Assembly Verification of Protein Particles

To analyze the structure of the recombined protein particles prepared according to Example 2, the recombined protein particles were photographed using a transmission electron microscope (TEM). First, an unstained, purified protein sample was placed on a carbon-coated copper electron microscope grid, and then naturally dried. To obtain stained protein particle images, the electron microscope grid including the naturally dried sample was incubated together with a 2% (w/v) aqueous uranyl acetate solution at room temperature for 10 minutes, followed by washing with distilled water three to four times.

To obtain an image of aggregates in which Au particles were gathered, a sample of a color-changed assay solution used for diagnosis was placed on a grid and then naturally dried without a separate staining process.

Protein particles and Au particle aggregate were observed using an electron microscope, Philips Technai 120 kV. As results, it was confirmed that the respective protein particles were spherical and the respective Au particle aggregates were radial (FIGS. 1, 4, 8 and 11).

Example 4

One-Step Diagnosis Using Signal Self-Amplification 4-1. Disease-Specific Marker Detection Through Antigen Detection In the case of acute myocardial infarction (AMI), 200 μL of a goat anti-TnI polyclonal IgG (cat. no. 70-XG82, Fitzgerald, Acton, Mass., U.S.A) antibody at a concentration of 1 mg/ml was added to 800 μL of $H_6$-$SPA_B$-capsid protein particles manufactured according to Example 2 and adjusted to a concentration of 1.25 mg/ml, followed by mixing at 4° C. for 12 to 16 hours to be bound to each other.

To the protein particles to which the antibody has been fixed, 500 μL of 0.5% (w/v) $Au^{3+}$ion solution ($HAuCl_4$ (cat. no. 254169, Sigma Aldrich, St. Louis, Mo., U.S.A.) was added, followed by mixing at 4° C. for 12 to 16 hours to be bound to each other.

60 μL of the solution (pre-assay solution) including the protein particles to which the antibody and the Au ions had been fixed was fed into each well of a 96-well plate (cat. no. 3599, Costar, N.Y., U.S.A.), and then 20 μL of a serum sample of a patient with AMI or a normal individual was added thereto. Soon after addition of the serum sample, 20 μL of 0.05 M L-ascorbic acid (cat. no. A7506, Sigma Aldrich, St. Louis, Mo., U.S.A.), as a reducing agent, was added thereto to induce signal self-amplification. As a result, it was confirmed that a chromogenic reaction occurred in the well to which the patient serum sample had been added within 5 minutes (FIG. 2A).

In addition, it was confirmed that such a color change occurred due to a high absorbance at a wavelength band of 576 nm. In addition, an absorbance difference between the patient serum and the normal individual serum at the wavelength band was confirmed using a microplate reader (Infinite M200 Pro, TECAN, Zurich, Switzerland) (FIG. 2 B).

4-2. Disease-Specific Marker Detection Through Antibody Detection

1) Human Hepatitis C virus (HCV) Diagnosis

In the case of HCV, 250 μL of $H_6$-c33c-capsid protein particles at a concentration of 2.0 mg/ml and 250 μL of $H_6$-hFTN-511p-c100p-c22p protein particles at a concentration of 1.0 mg/ml were added to 500 μL of $H_6$-SPA $_B$-capsid protein particles at a concentration of 1.0 mg/ml manufactured according to Example 2, thereby preparing a protein particle mixture solution. Next, 500 μL of 0.5% $Au^{3+}$ion solution was added thereto, followed by mixing at 4° C. for 12 to 16 hours to be bound to each other.

60 μL of the prepared solution (pre-assay solution) was added to each well of a 96 well plate, and 20 μL of a serum sample of a patient with hepatitis C or a normal individual was added thereto. Soon after addition of the serum sample, 20 μL of 0.05 M L-ascorbic acid was added thereto to induce signal self-amplification. As a result, it was confirmed that a chromogenic reaction occurred in the well to which the patient serum sample had been added within 5 minutes (FIG. 10A).

In addition, it was confirmed that such a color change occurred due to a high absorbance at a wavelength band of 588 nm. In addition, an absorbance difference between the patient serum and the normal individual serum at the wavelength band was confirmed using a microplate reader (FIG. 10B).

2) Human Immunodeficiency Virus (HIV) Diagnosis

In the case of HIV, an experimental procedure was the same as that in HCV, but the composition of a protein particle mixture solution was different. That is, 250 µL of H$_6$-gp41-capsid protein particles at a concentration of 3.0 mg/ml and 250 µL of H$_6$--p24-capsid protein particles at a concentration of 1.0 mg/ml were added to 500 µL of H$_6$-SPA B-capsid protein particles at a concentration of 1.0 mg/ml, thereby preparing a protein particle mixture solution. Next, 500 µL of 0.5% Au$^{3+}$ ion solution was added thereto, followed by mixing at 4° C. for 12 to 16 hours to be bound to each other.

60 µL of the prepared solution (pre-assay solution) was added to each well of a 96 well plate, and 20 µL of a serum sample of a patient with HIV or a normal individual was added thereto. Soon after addition of the serum sample, 20 µL of 0.05 M L-ascorbic acid was added thereto to induce signal self-amplification. As a result, it was confirmed that a chromogenic reaction occurred in the well to which the patient serum sample had been added within 5 minutes (FIG. 11).

3) Human Hepatitis A Virus(HAV) Diagnosis

In the case of HAV, 200 pt of hFTN-epl-H$_6$ protein nanoparticles at a concentration of 2.0 mg/ml, 200 µL of hFTN-ep2-H$_6$ protein nanoparticles at a concentration of 2.0 mg/ml, and 200 µL of hFTN-ep3-H$_6$ protein nanoparticles at a concentration of 1.0 mg/ml were added to 600 µL of H$_6$-SPA B-capsid protein particles at a concentration of 1.0 mg/ml manufactured according to Example 2, thereby preparing a protein particle mixture solution. Next, 600 µL of 0.5% Au$^{3+}$ ion solution was added thereto, followed by mixing 4° C. for 12 to 16 hours to be bound to each other.

Figure 12:
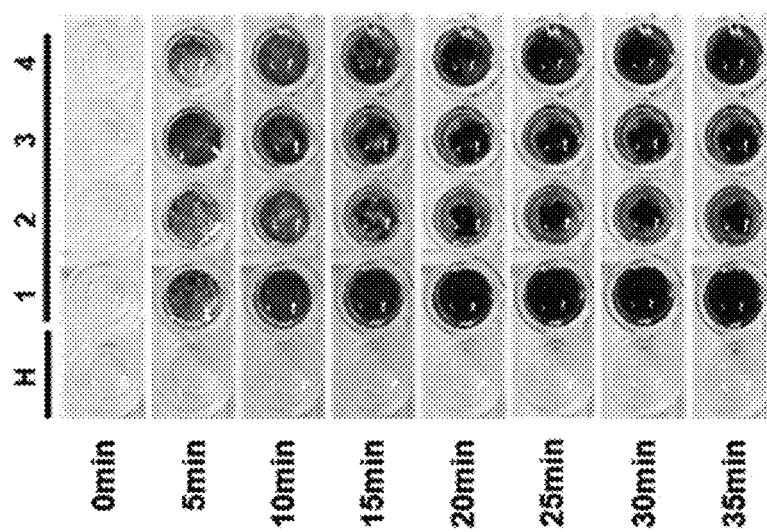
In FIG. 12, a left panel illustrates test results of blood samples of a patient with HAV and a normal individual according to the method of the present invention, and a right panel illustrates antigen-antibody complex size-dependent absorbances and time-dependent absorbance changes in the patient with HAV. Particularly, it is illustrated that an absorbance increases at a specific wavelength of 574 nm over time.
Figure 12:
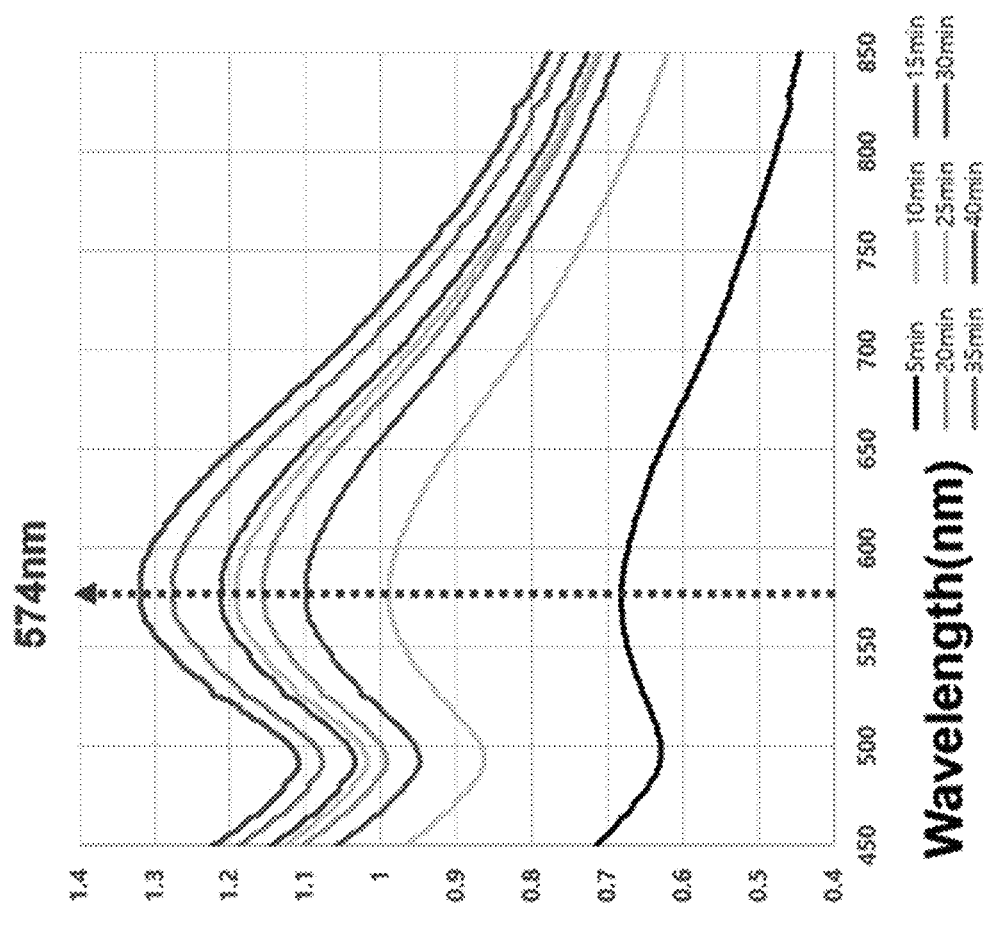

60 µL of the prepared solution (pre-assay solution) was added to each well of a 96 well plate, and 20 µL of a serum sample of a patient with hepatitis A or a normal individual was added thereto. Soon after addition of the serum sample, 20 µL of 0.05 M L-ascorbic acid was added thereto to induce signal self-amplification. As a result, it was confirmed that a chromogenic reaction occurred in the well to which the patient serum sample had been added within 5 minutes (FIG. 12).

Example 5

ELISA and ECLIA Experiments Using Controls

A serum sample of a patient with AMI was subjected to ELISA and ECLIA, compared to controls. In ELISA, a kit (Abbexa, U.K., abx252868) having a detection limit of 12.5 pg/ml was used. In ECLIA, a kit having a detection limit of 0.16 ng/ml was used (Modular Analytics E170, Roche, Germany).

Figure 3:
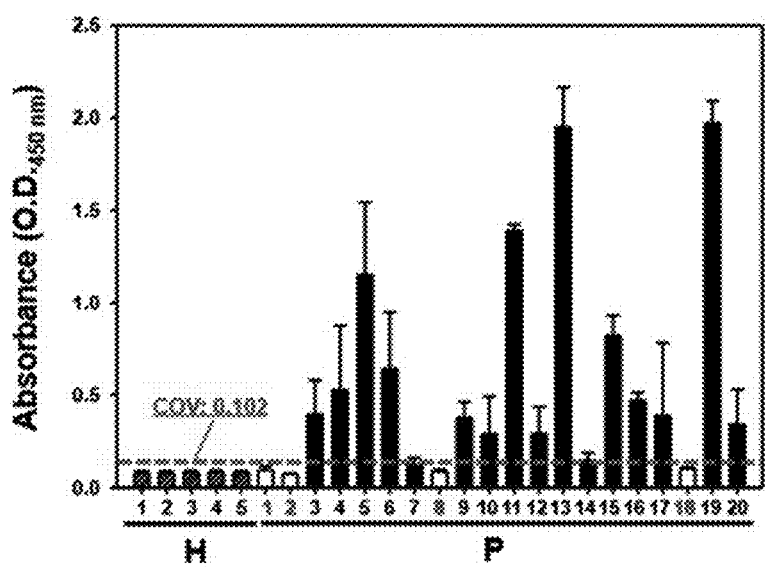
FIG. 3(A) illustrates experiment results of diagnose of serum of the same patient using an ELISA kit for detecting a marker, troponin I, for acute myocardial infarction.
FIG. 3(B) illustrates results (upper panel) obtained by additionally quantifying the amount of troponin I in the patient serum by ECLIA at the Green Cross diagnostic center and results (lower panel) of one-step diagnosis using the patient serum to investigate the possibility of quantification.
Figure 3:
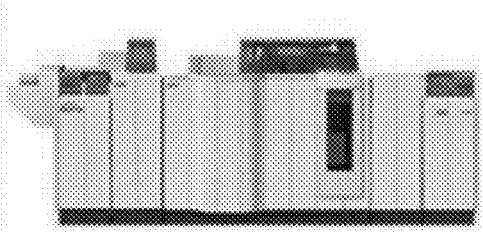
Figure 3:
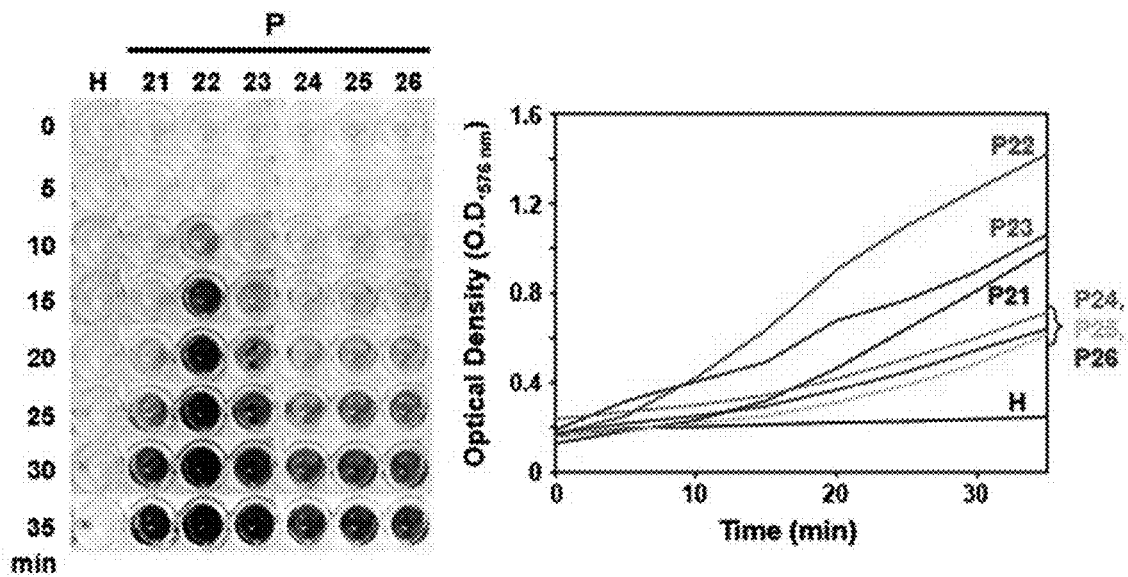
Figure 4:
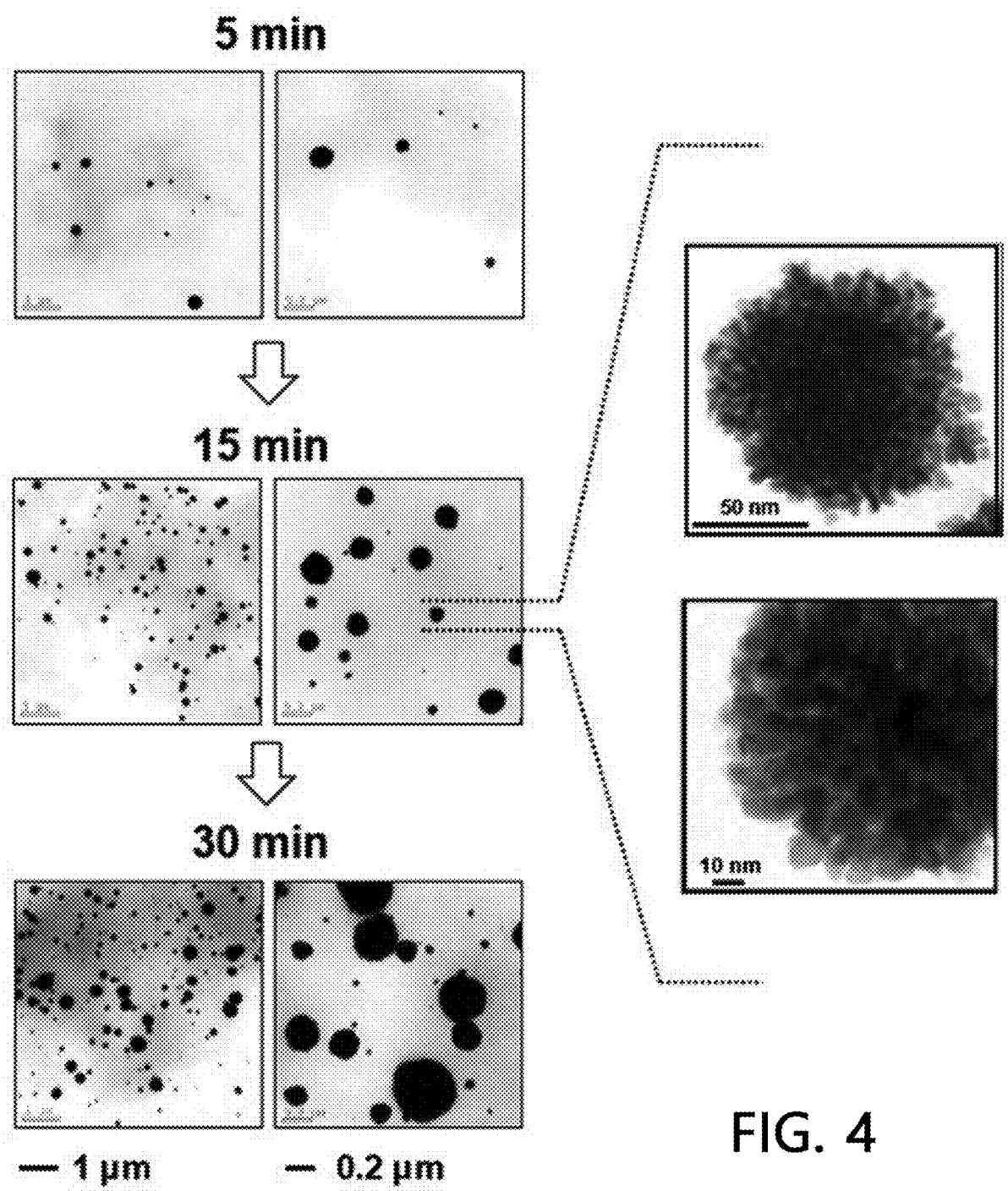
FIG. 4 illustrates TEM images of Au particle aggregates in an assay solution of a patient at each time zone.

The same serum samples from 20 patients were used. From resultant experimental results, it was confirmed that one-step diagnosis using self-signal amplification was more sensitive, more rapid, and more accurate (FIG. 3)

Example 6

Au Nanoaggregate Model Simulation Experiment

In the one-step diagnosis experiment performed in Example 4, it was confirmed that a color rapidly turned blue in a patient. To investigate the cause of such a change, an finite difference time domain (FDTD) simulation experiment (Lumerical Solutions, ver. 8.15.736) was performed.

Figure 5:
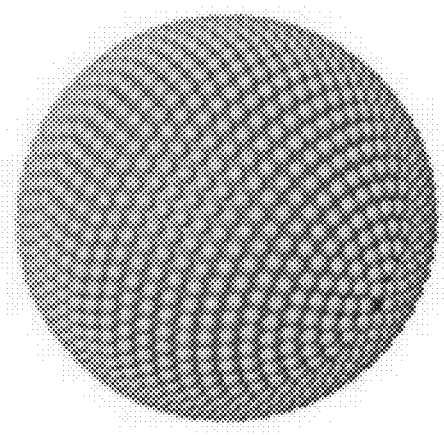
FIG. 5(A) illustrates a simulation result of the principle that Au particle aggregates are formed.
FIG. 5(B) illustrates that absorbance increases in proportion to the size of an aggregate, particularly that the pattern wherein absorbance increases in proportion to the size of aggregate occurs at the same wavelength band.
Figure 5:
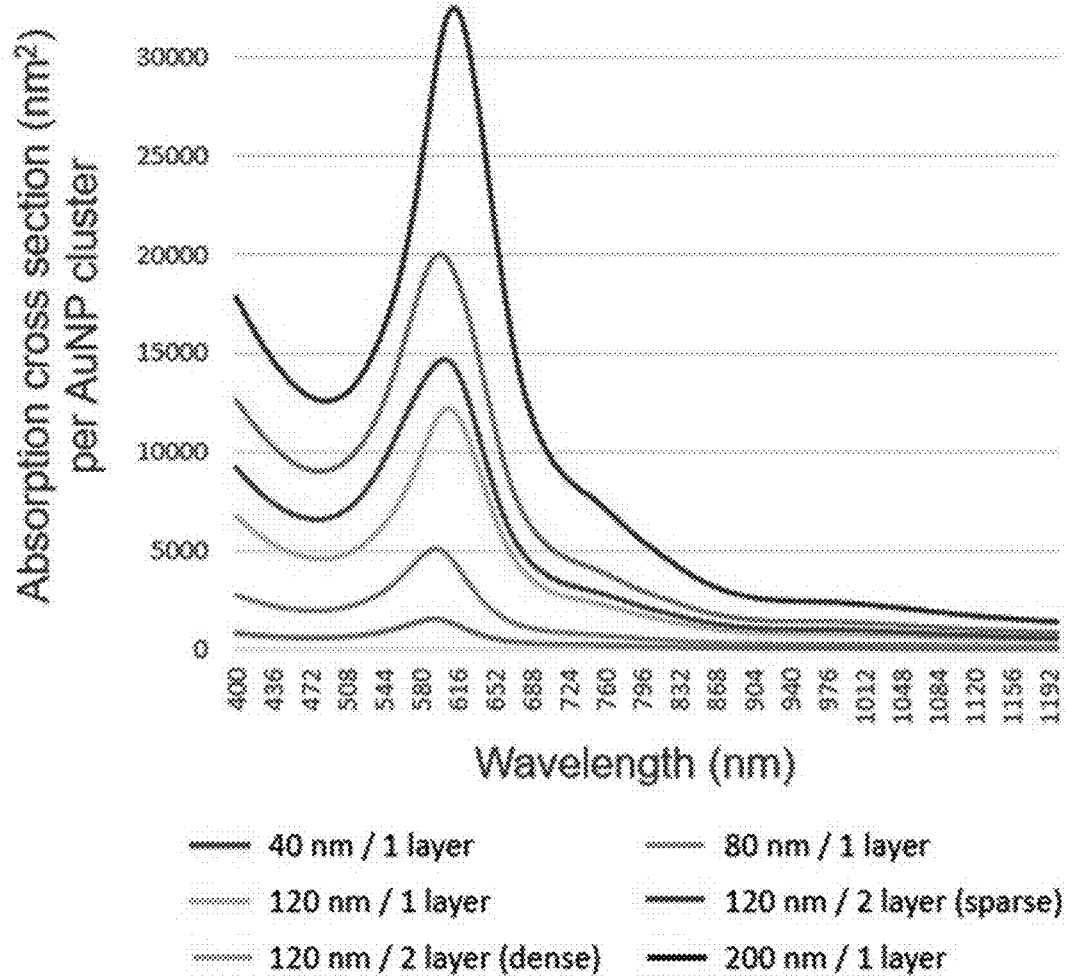

As a result of the simulation, a raspberry-shaped protein-metal complex as illustrated in FIG. 5A is formed. When the sizes of the aggregates were changed under the assumption that aggregates are formed in the form, a change in an absorption cross-sectional area was shown according to a wavelength in FIG. 5B. An absorption cross-sectional area was obtained by dividing the absorption power stored in a surrounding area including particles by the intensity of a light source.

In addition, in the case of the raspberry-shaped simulation model shown in FIG. 5A, it was confirmed that, as the sizes of aggregates increased, an absorbance increased in the same wavelength band rather than being separated into different wavelengths (FIG. 5B). This was confirmed as coinciding with an actual one-step diagnosis result.

Example 7

Control Experiment for Analyzing Principle of One-Step Diagnosis Experiment

Figure 6:
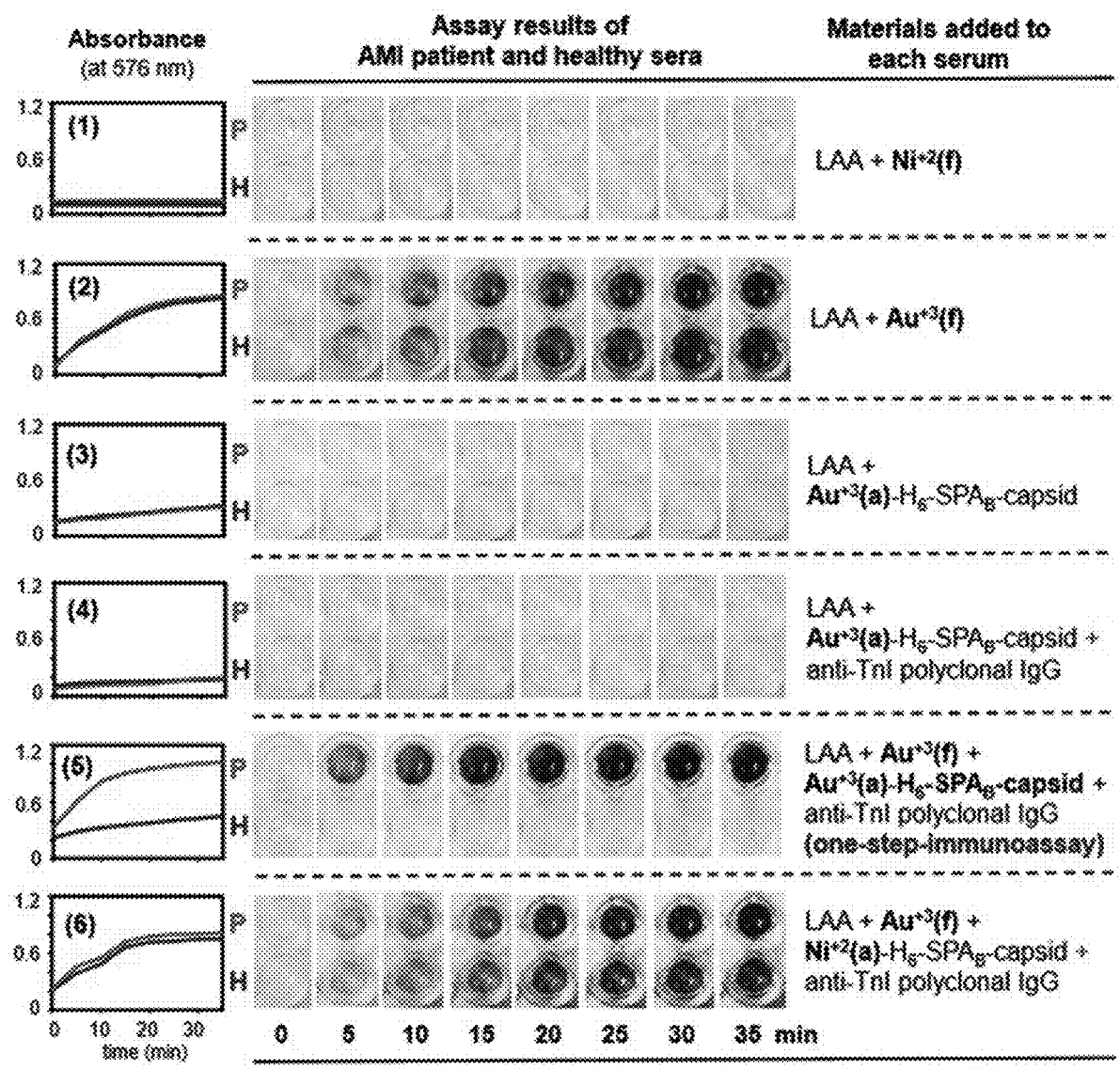
FIG. 6 illustrates results of control experiments for investigating the principle of one-step diagnosis, particularly that complexes are generated when free Au ions are present and antigen-antibody complexes due to protein particles are formed, and thus, a chromogenic reaction occurs only in a patient (5).
Figure 7:
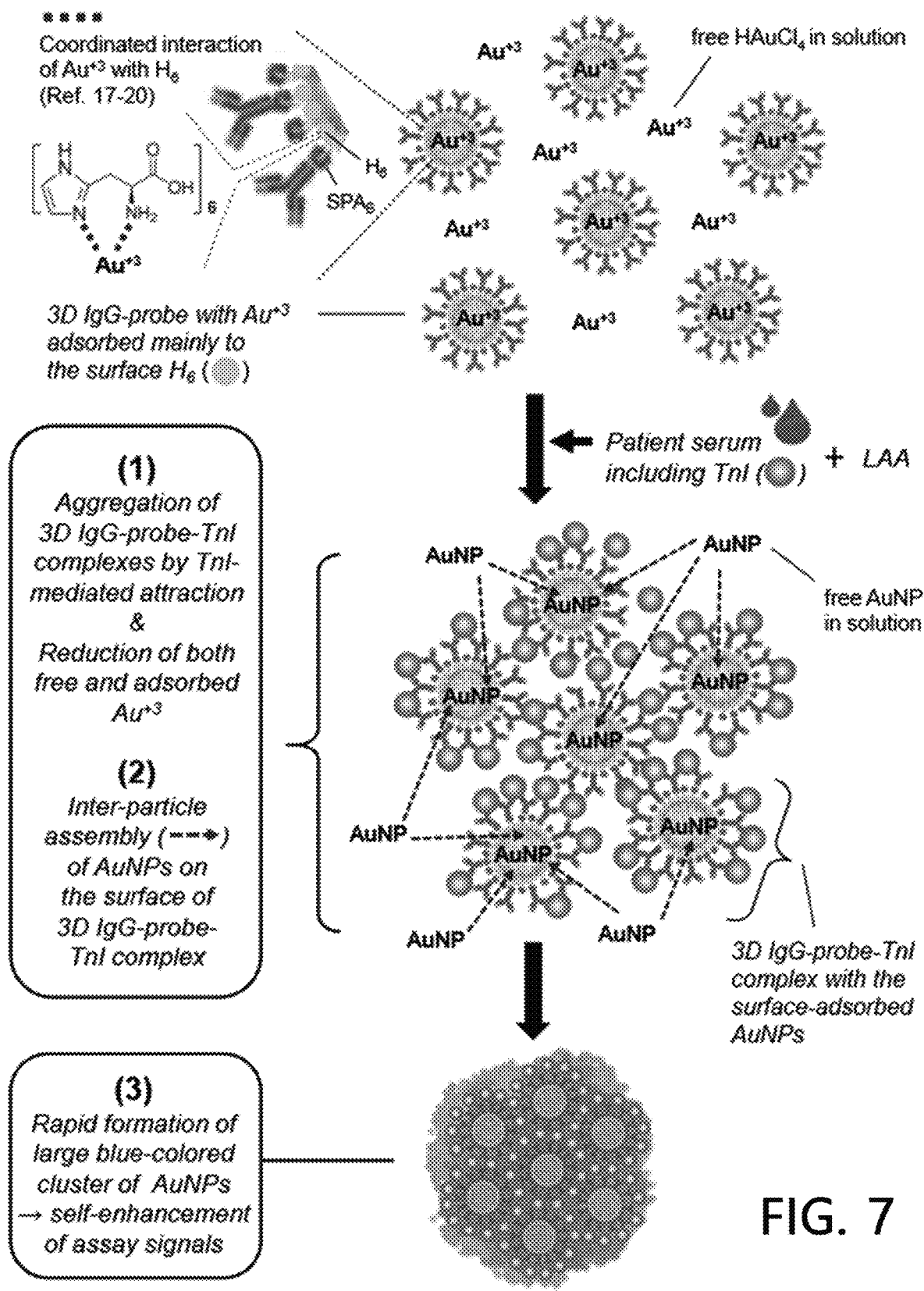
FIG. 7 is a schematic diagram illustrating an interaction between Au ions and reducible peptides, an interaction between troponin I and protein particles in a patient sample, and how a signal self-amplification action due to the interactions occurs in this diagnosis.

A control experiment was preformed to analyze the principle of one-step diagnosis. To perform a control experiment, Ni$^{2+}$, which is known to well bind histidine that is an amino acid binding to Au ions, was attached to histidine of protein particles. From the experimental results, it was confirmed whether binding between Au ions and histidine of protein particles affected this experiment, and the one-step diagnosis experiment was smoothly performed when the amount of gold ions freely present in a solution, as well as gold ions attached to protein particles, was a certain amount or more (FIGS. 6 and 7).

Experimental conditions of each number of FIG. 6 were as follows:

1: An experimental group to confirm whether, by simply treating with a Ni$^{2+}$ solution, a patient serum, a normal individual serum, and a reducing agent, LAA, without any substance treatment, Ni$^{2+}$ meets LAA, and thus, a color appeared while being reduced 2: A color change was measured by simply treating with an Au$^{3+}$ (gold ions) solution, a patient serum, a normal individual serum, and a reducing agent, LAA, without any other substance treatment. As a result, it was confirmed that gold ions were reduced and turned blue while forming particles, regardless of the patient and the normal individual.

3: Only Au ions were attached to protein particles, and a patient serum, a normal individual serum, and a reducing agent were treated. As a result, since there were no free Au ions, there was no color change in the both serum samples.

4: An antibody was attached to protein particles, and then Au ions were attached thereto. Next, a patient serum, a normal individual serum, and a reducing agent were treated. To compare to the case 3 wherein there was no antibody, an experiment of binding an antibody was performed. As a result, it was confirmed that, since there were no free Au ions, color change did not occur.

5: As a result of reproducing an existing diagnosis method, it was confirmed that a color change occurred only in the patient serum.

6: To prevent Au ions from adhering to protein particles to which an antibody had been attached, the protein particles were previously treated with Ni$^{2+}$ ions and free ions were present in the protein particles. These protein particles were treated with a patient serum, a normal individual serum, and a reducing agent. As a result, it was confirmed that reduction occurred due to the free ions, and thus, a color change occurred. However, it was confirmed that, since Au ions were absent in the protein particles to which the antibody had been attached, cluster formation was not facilitated, and thus, there was no difference between the normal individual serum and the patient serum.

Example 8

Confirmation of Reliability of Quantitative Analysis Using One-Step Diagnosis Experiment and Known Diagnosis Kit 8-1. Confirmation of Possibility of Quantitative Analysis of One-Step Diagnosis Method of Present Invention A human serum-derived TnI standard sample (30-AT43, Fitzgerald, Acton, Mass., U.S.A.) was respectively spiked to three types of normal individual serums, standard serum samples at different concentrations (0, 2, 5, 10, 20, 30 ng/ml) were prepared for each of the normal individual serums, and detection signals of the serums were detected as an absorbance at 576 nm at 15 minutes (FIG. 13A), 20 minutes (B), 25 minutes (C) and 30 minutes (D) after the start of diagnosis according to the method of Example 4.

Figure 13:
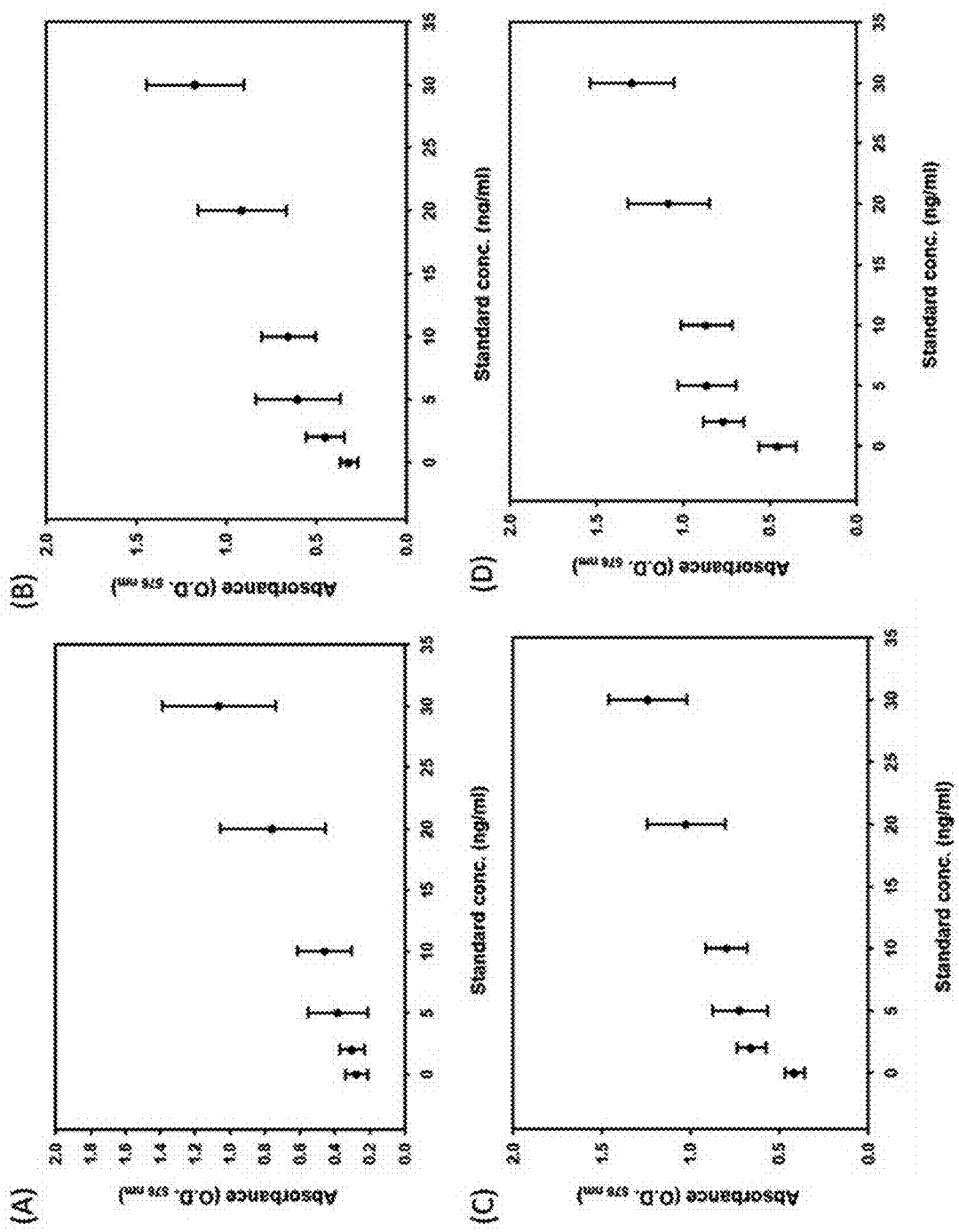
FIG. 13 illustrates a test result of evaluating whether quantitative analysis of TnI in patient serum is reliable. (A) illustrates an absorbance measurement result of each standard serum 15 minutes after the start of diagnosis, (B) illustrates detection signal measurement results 20 minutes after the start of diagnosis, (C) illustrates detection signal measurement results 25 minutes after the start of diagnosis, and (D) illustrates detection signal measurement results 30 minutes after the start of diagnosis.

As results, as shown in FIG. 13, it was confirmed that linear proportionalities of measured detection signal values were the best at 15 minutes and 20 minutes after the start of diagnosis. In addition, at 15 to 20 minutes after the start of diagnosis, it was confirmed that a disease was developed or not and quantitative analysis was possible.

Figure 14:
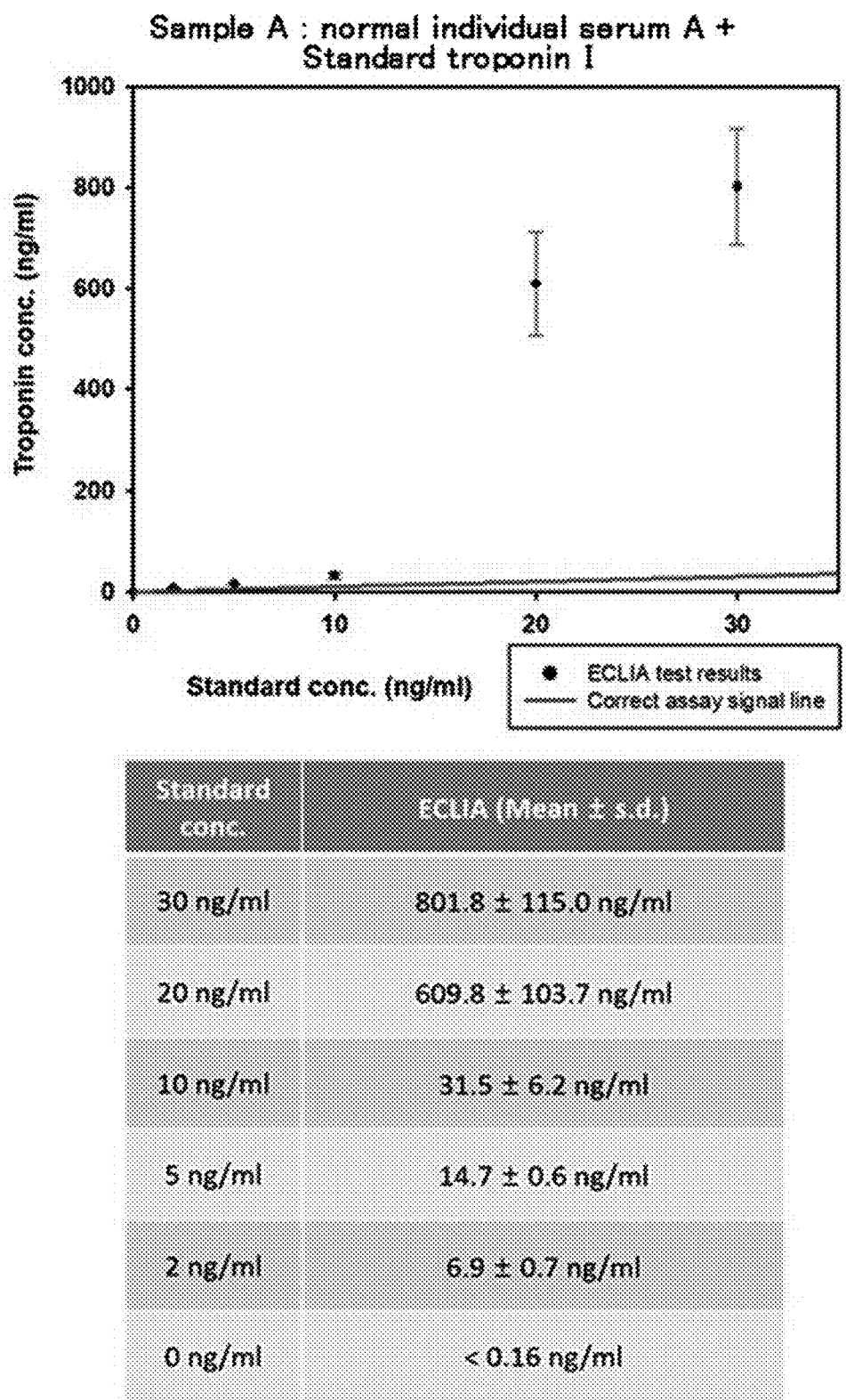
FIGS. 14 to 16 illustrate results of quantitative analysis performed using the ECLIA diagnostic device (model name: Roche E-170) of the Green Cross Medical Foundation. Particularly.
Figure 15:
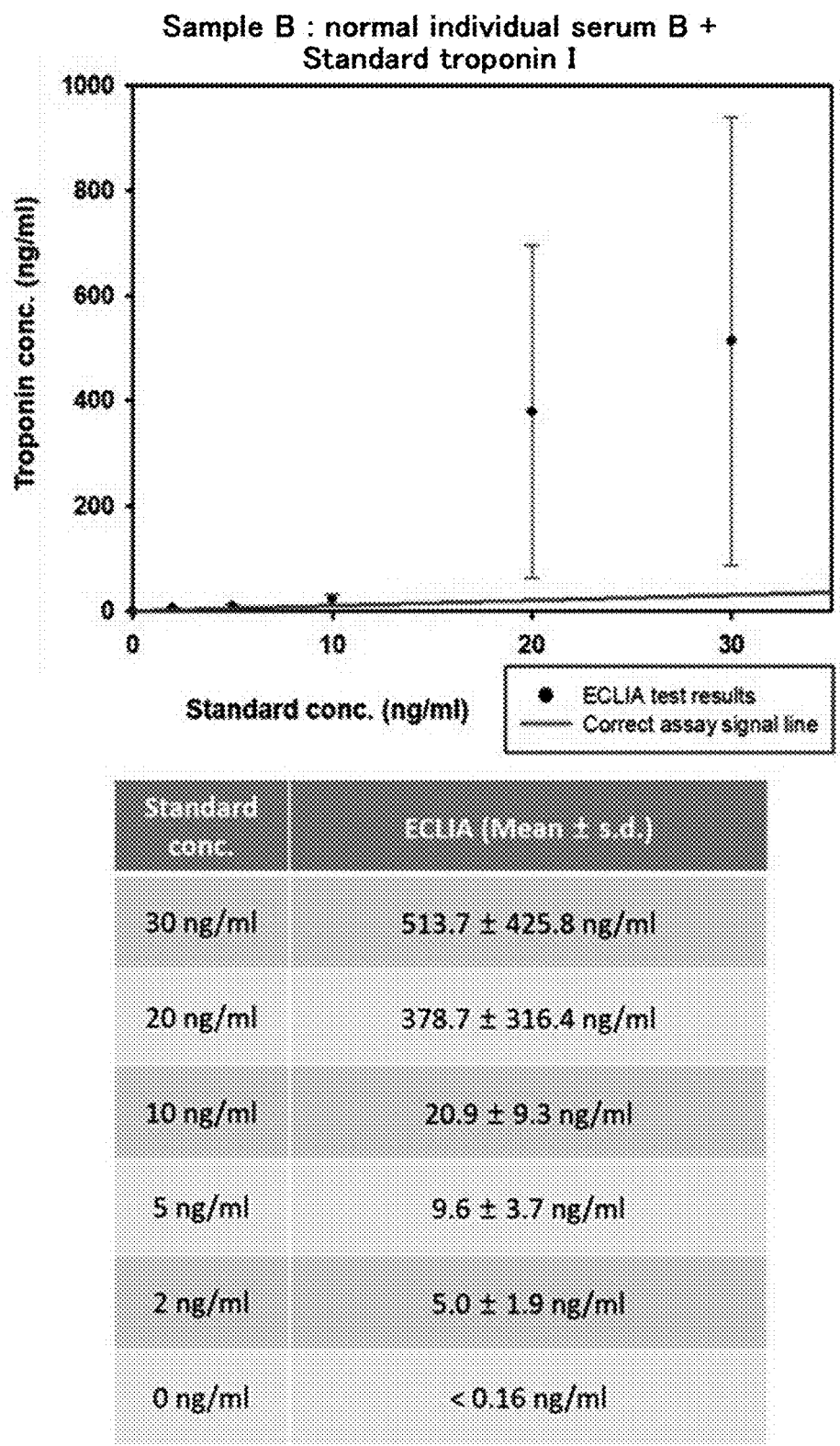
Figure 16:
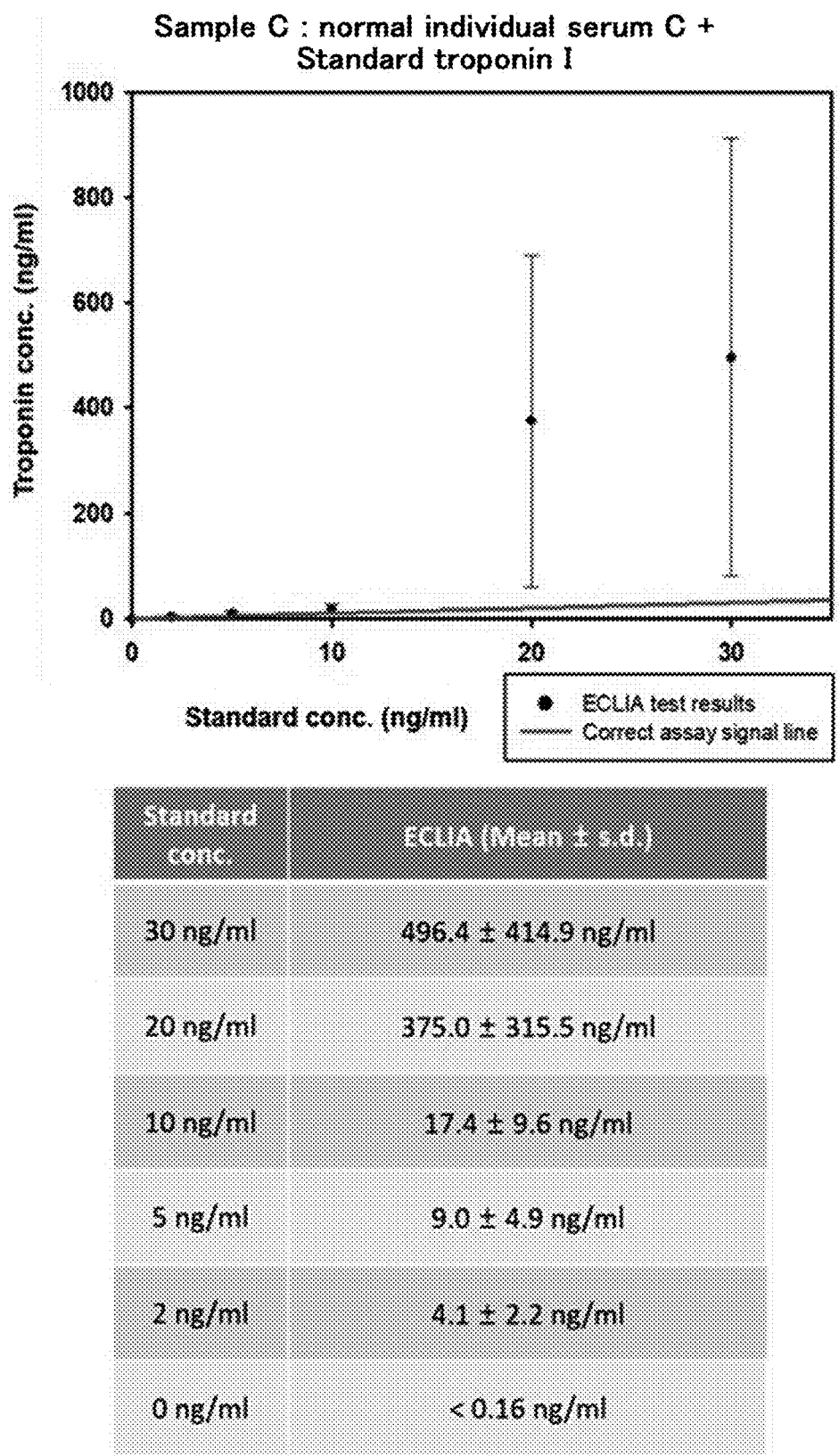

8-2. Confirmation of Possibility of Quantitative Analysis of Known Diagnosis Kit 1) ECLIA Diagnosis Equipment Provided by Green Cross Medical Foundation Using an ECLIA diagnosis equipment (Roche E-170 model) provided by the Green Cross Medical Foundation, standard serum samples (normal individual sample A: FIG. 14, normal individual sample B: FIG. 15, normal individual sample C: FIG. 16) prepared according to Example 8-1 were subjected to quantitative analysis.

As results, as shown in FIGS. 14 to 16, it was confirmed that an exaggerated analysis result tended to be shown as the actual concentration of TnI increased, such a tendency increased at a concentration of 20 ng/ml or more, and variations between measured values also varied greatly for each sample.

2) ELISA Diagnosis Equipment Manufactured by Elabscience

Figure 17:
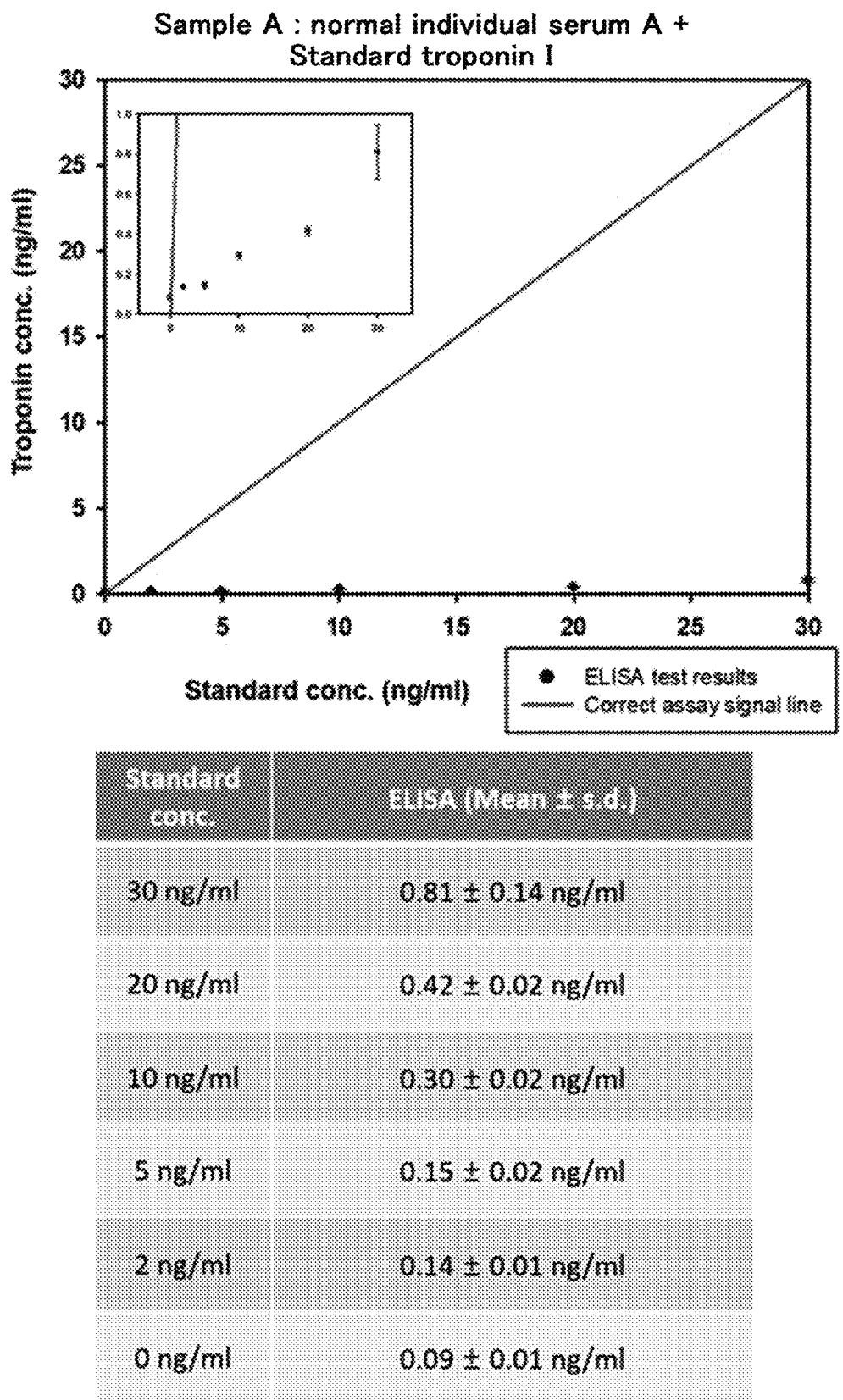
FIGS. 17 to 19 illustrate results of quantitative analysis performed using an ELISA diagnosis kit (E-EL-H0144) manufactured by Elascience. Particularly.
Figure 18:
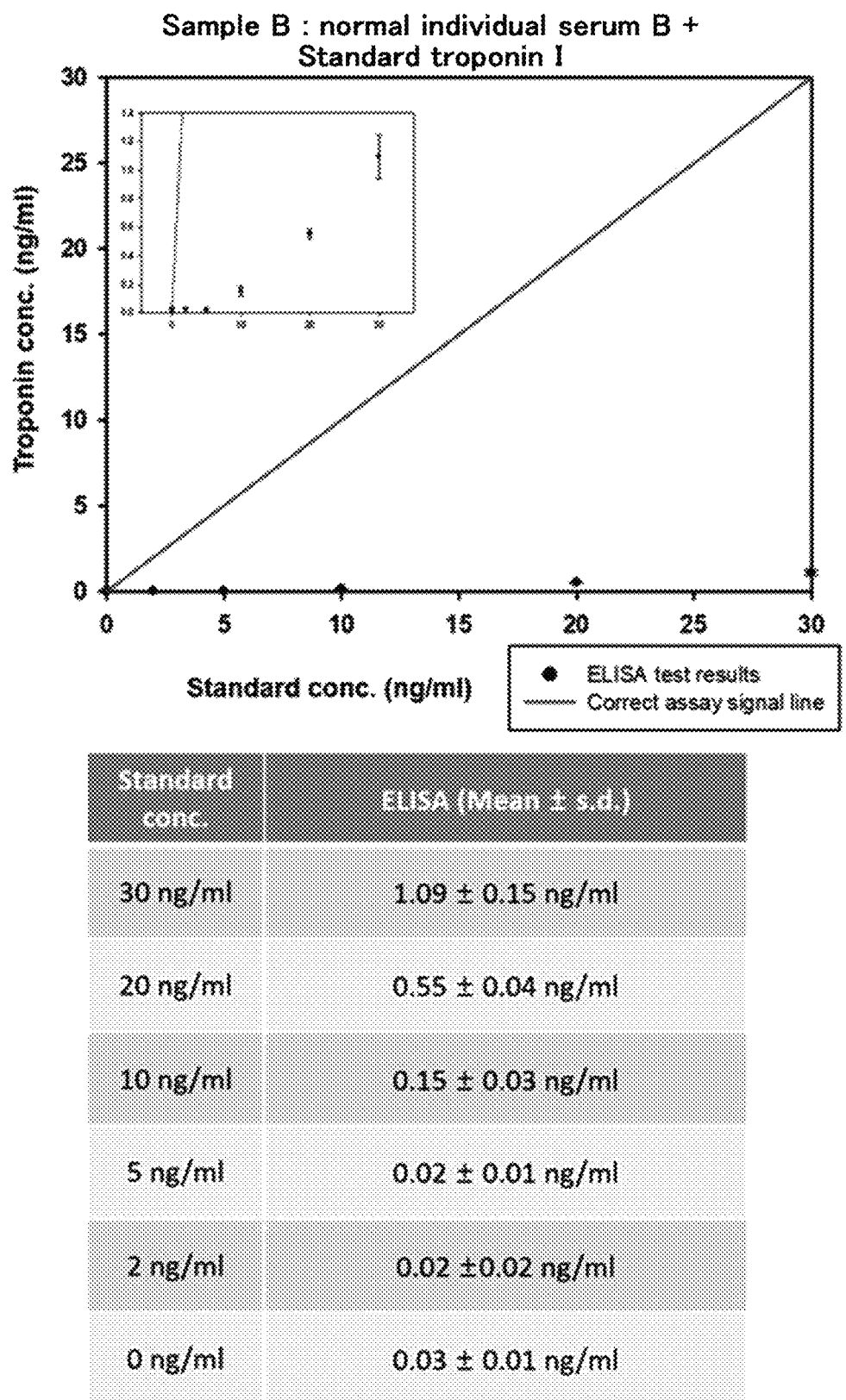
Figure 19:
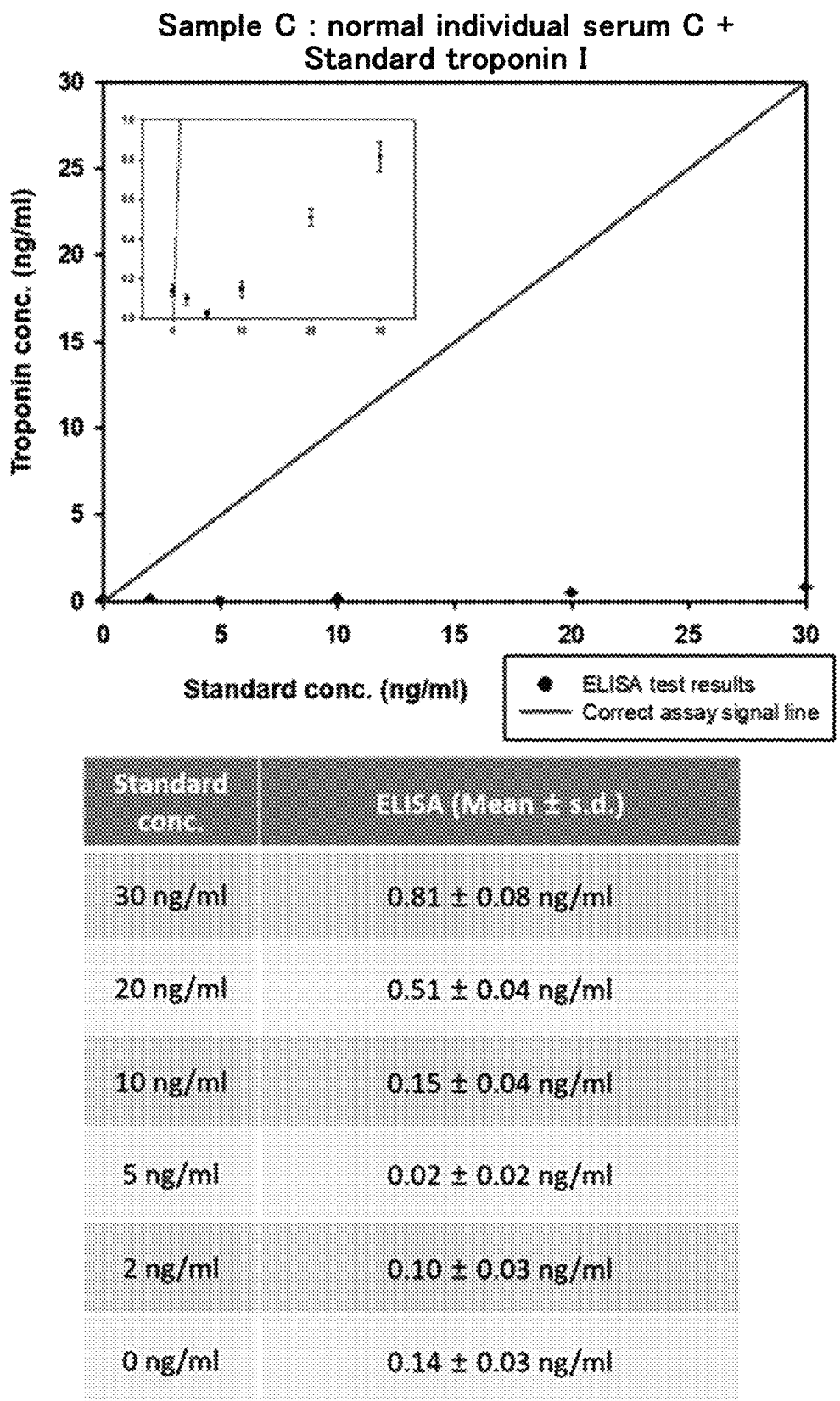

Using a diagnosis equipment (E-EL-H0144, Elabscience, 14780 Memorial Drive, Suite 216, Houston, Tex. 77079, U.S.A.) manufactured by Elabscience, standard serum samples (normal individual sample A: FIG. 17, normal individual sample B: FIG. 18, normal individual sample C: FIG. 19) prepared according to Example 8-1 were subjected to quantitative analysis.

As results, as shown in FIGS. 17 to 19, it was confirmed that, contrary to the analysis results by the ECLIA diagnosis equipment, detection signals lower than actual concentrations were measured in all serum samples, and there was no deviation, but there was no reliable concentration interval.

3) ELISA Diagnosis Equipment Manufactured by Abbexa

Figure 20:
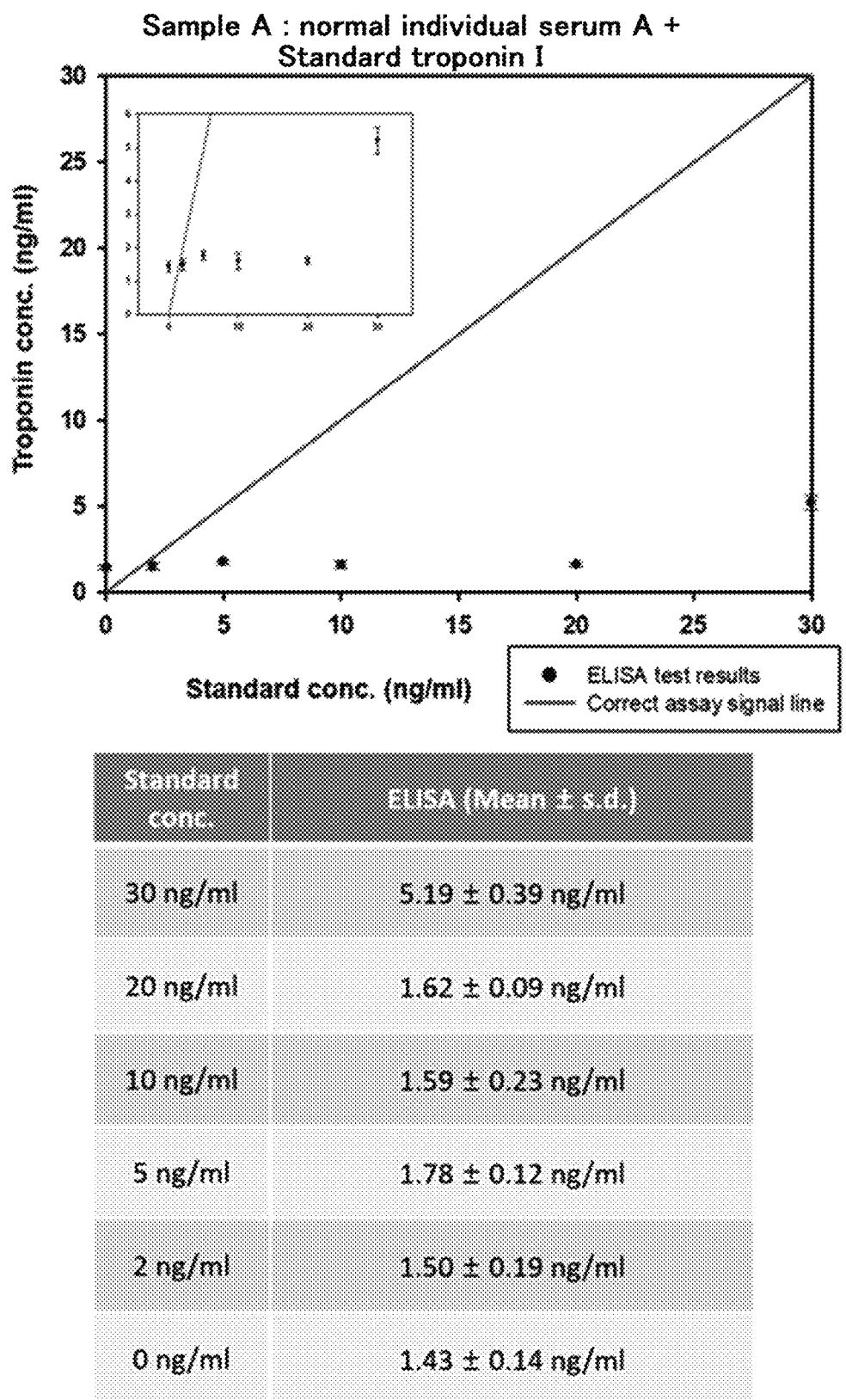
FIGS. 20 to 22 illustrate results of quantitative analysis performed using an ELISA diagnosis kit (abx050255) manufactured by Abbexa Ltd. Particularly.
Figure 21:
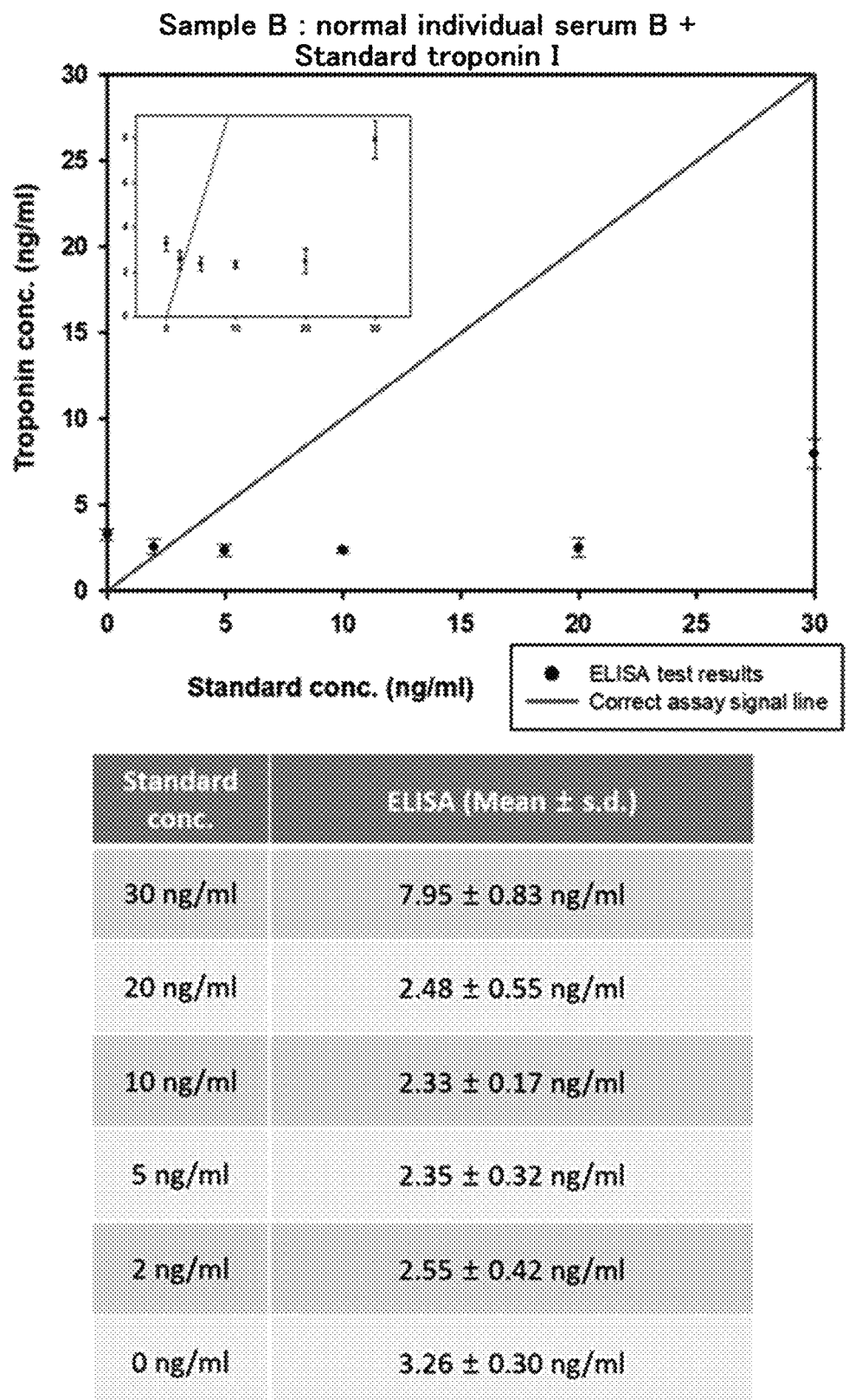
Figure 22:
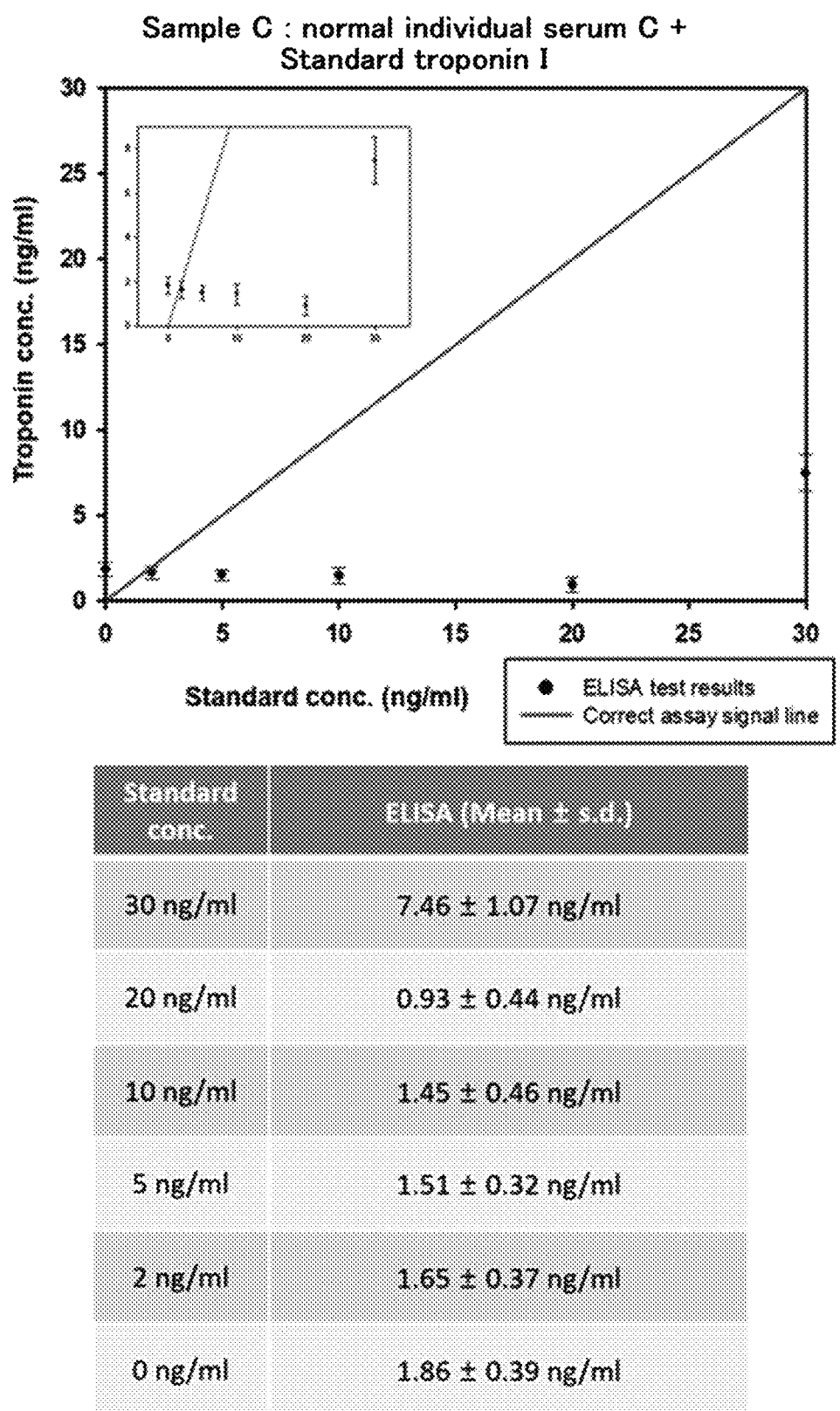

Using a diagnosis equipment (abx050255, Abbexa Ltd. Cambridge Science Park, Cambridge, CB4 OEY, U.K.) manufactured by Abbexa, standard serum samples (normal individual sample A: FIG. 20, normal individual sample B: FIG. 21, normal individual sample C: FIG. 22) prepared according to Example 8-1 were subjected to quantitative analysis.

As results, as shown in FIGS. 20 to 22, it was confirmed that, similar to the diagnosis results by the ELISA diagnosis equipment manufactured by Elabscience, detection signals lower than actual concentrations were measured, and there was no proportionality of measured signal measured values according to a concentration, whereby reliable quantitative analysis results were obtained.

4) ELISA Diagnosis Equipment Manufactured by ALPCO

Figure 23:
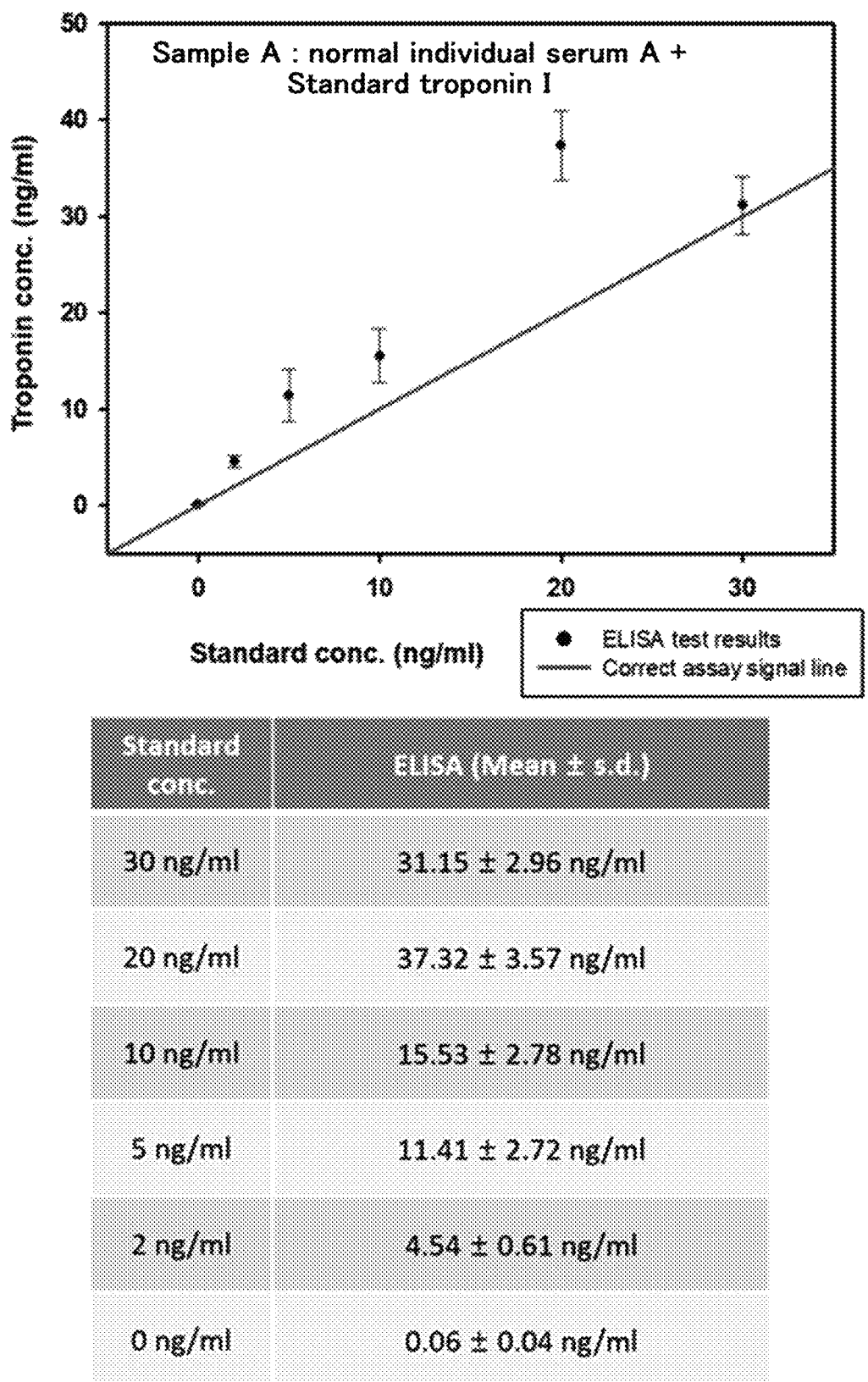
FIGS. 23 to 25 illustrate results of quantitative analysis performed using an ELISA diagnosis kit (25-TR1HU-E01) manufactured by ALPCO. Particularly.
Figure 24:
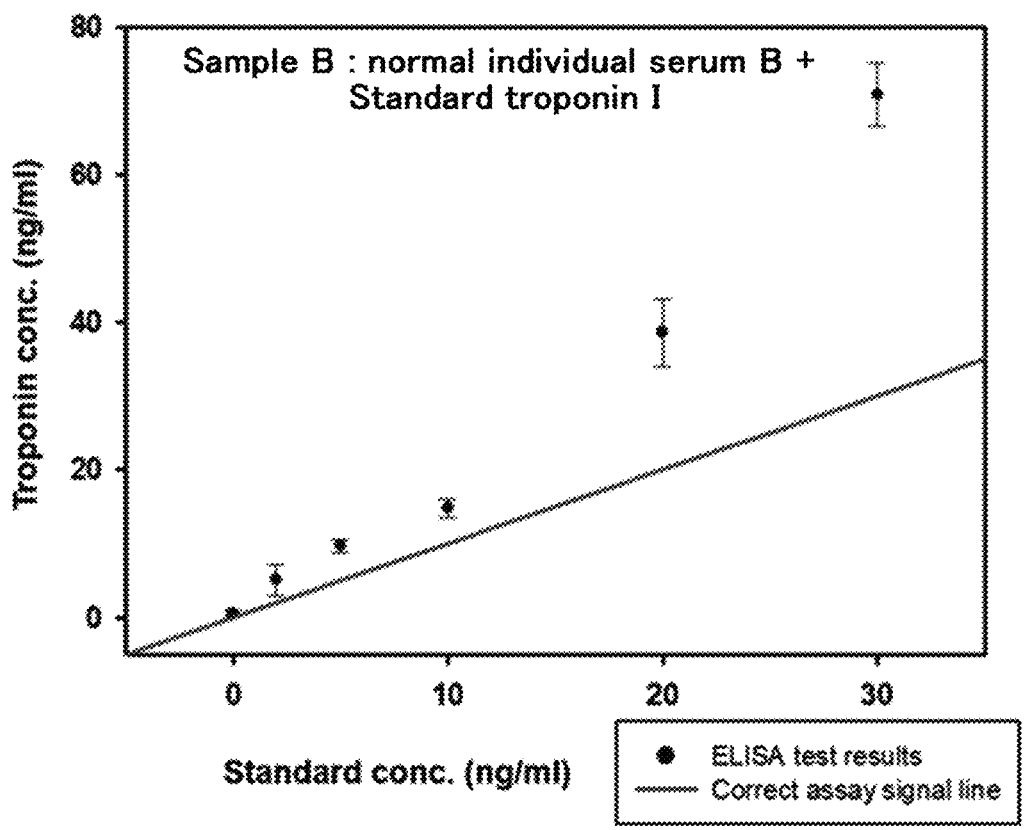
Figure 25:
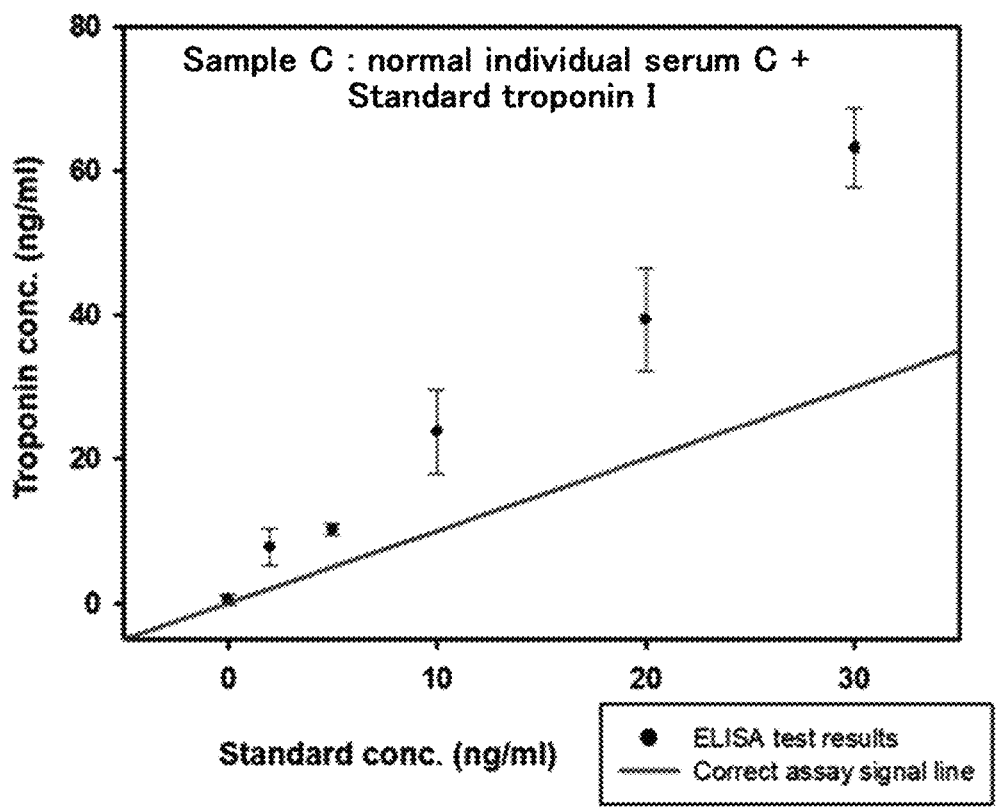

Using a diagnosis equipment (25-TR1HU-E01, ALPCO. 26-G Keewaydin Drive, Salem, N.H. 03079, U.S.A.) manufactured by ALPCO, standard serum samples (normal individual sample A: FIG. 23, normal individual sample B: FIG. 24, normal individual sample C: FIG. 25) prepared according to Example 8-1 were subjected to quantitative analysis.

As results, as shown in FIGS. 23 to 25, it was confirmed that detection signals closet to actual concentrations were measured, compared the two types of ELISA diagnosis kits, but deviations in the entire concentration range were not small, and a linear proportionality according to concentrations was not high, whereby reliable quantitative analysis results were not obtained.

Example 9

Confirmation of Limit of Detection (LOD) of One-Step Diagnosis Method 9-1. Confirmation of LOD Upon Acute Myocardial Infarction Diagnosis A disease marker, Troponin I, in a concentration range of 0.002 to 2 ng/ml was spiked to a normal individual serum, thereby manufacturing a standard serum sample. The manufactured standard serum sample was subjected to the LOD measurement experiment of Example 4. A color changes in the sample in 96 well plate was confirmed and, simultaneously, an absorbance at 576 nm was measured.

Figure 26:
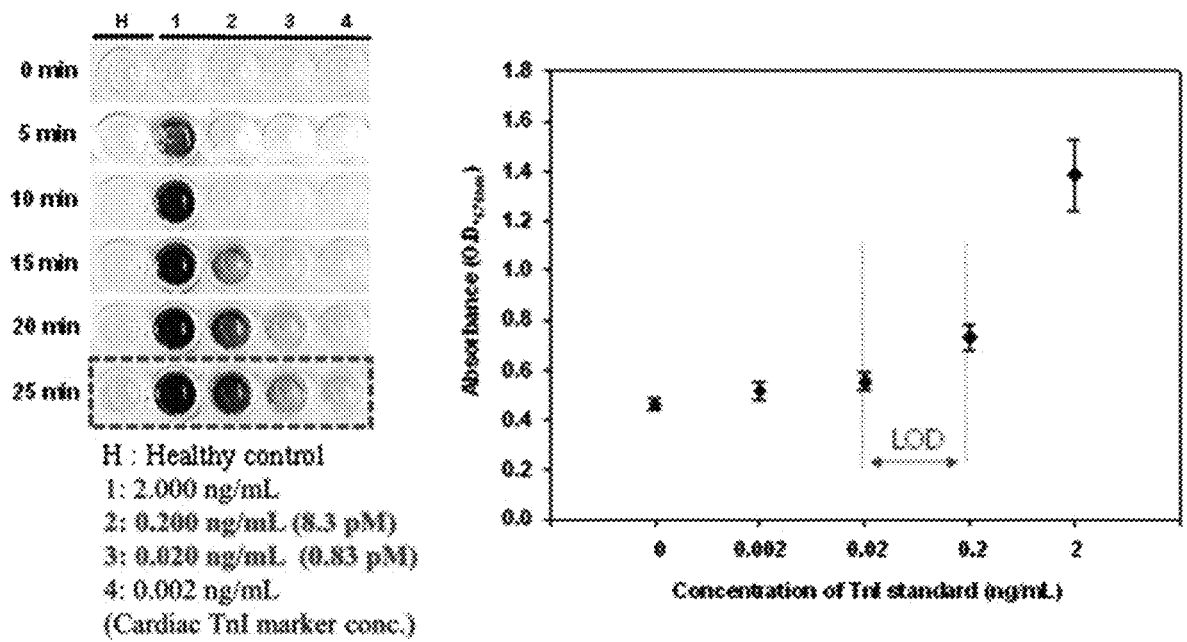
FIG. 26 illustrates quantification experiment results for evaluating the limit of detection (LOD) when diagnosing acute myocardial infarction using the method of the present invention.

As results, as shown in FIG. 26, it was confirmed that the LOD of TnI in the acute myocardial infarction diagnosis was present in a concentration range of at least 0.02 ng/ml (0.83 pM) and at most 0.2 ng/ml (8.3 pM). This was significantly low than the LOD (0.16 ng/ml) of the ECLIA-based diagnosis equipment.

9-2. Confirmation of LOD Upon Hepatitis C Diagnosis

A disease marker, anti-HCV(c33c) IgG standard (LS-C103178, LifeSpan BioSciences, Inc., Seattle, Wash., U.S.A.), in a concentration range of 0.001 to 10 ng/ml was spiked to a normal individual serum, thereby manufacturing a standard serum sample. The manufactured standard serum sample was subjected to the LOD measurement experiment of Example 4. A color changes in the sample in 96 well plate was confirmed and, simultaneously, an absorbance at 588 nm was measured.

Figure 27:
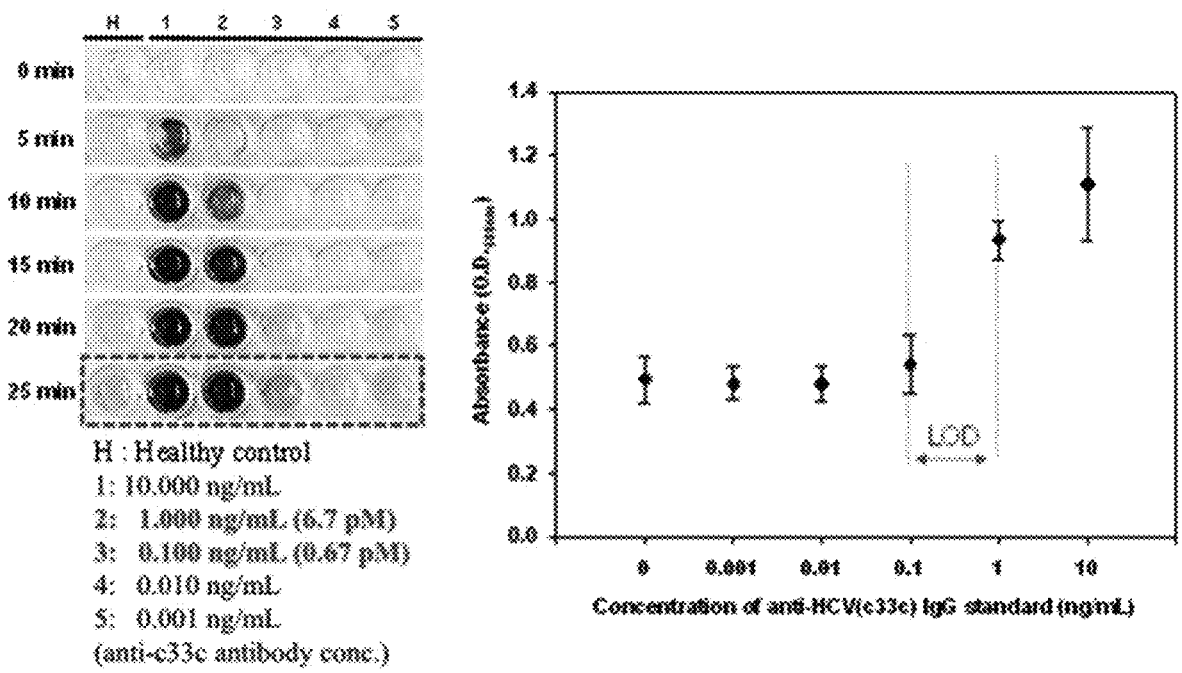
FIG. 27 illustrates quantification experiment results for evaluating the limit of detection (LOD) when diagnosing hepatitis C using the method of the present invention.

As results, as shown in FIG. 27, it was confirmed that the LOD of the anti-HCV antibody in the hepatitis C diagnosis was present in a concentration range of at least 0.1 ng/ml (0.67 pM) and at most 1.0 ng/ml (6.7 pM). This was significantly low than the LOD (nM level) of the ELISA-based diagnosis equipment.

9-3. Confirmation of LOD Upon AIDS Diagnosis

A disease marker, anti-HIV(gp41) IgG standard (2509, ImmunoDX, LLC., Woburn, Mass., U.S.A.), in a concentration range of 0.001 to 10 ng/ml was spiked to a normal individual serum, thereby manufacturing a standard serum sample. The manufactured standard serum sample was subjected to the LOD measurement experiment of Example 4. A color changes in the sample in 96 well plate was confirmed and, simultaneously, an absorbance at 555 nm was measured.

Figure 28:
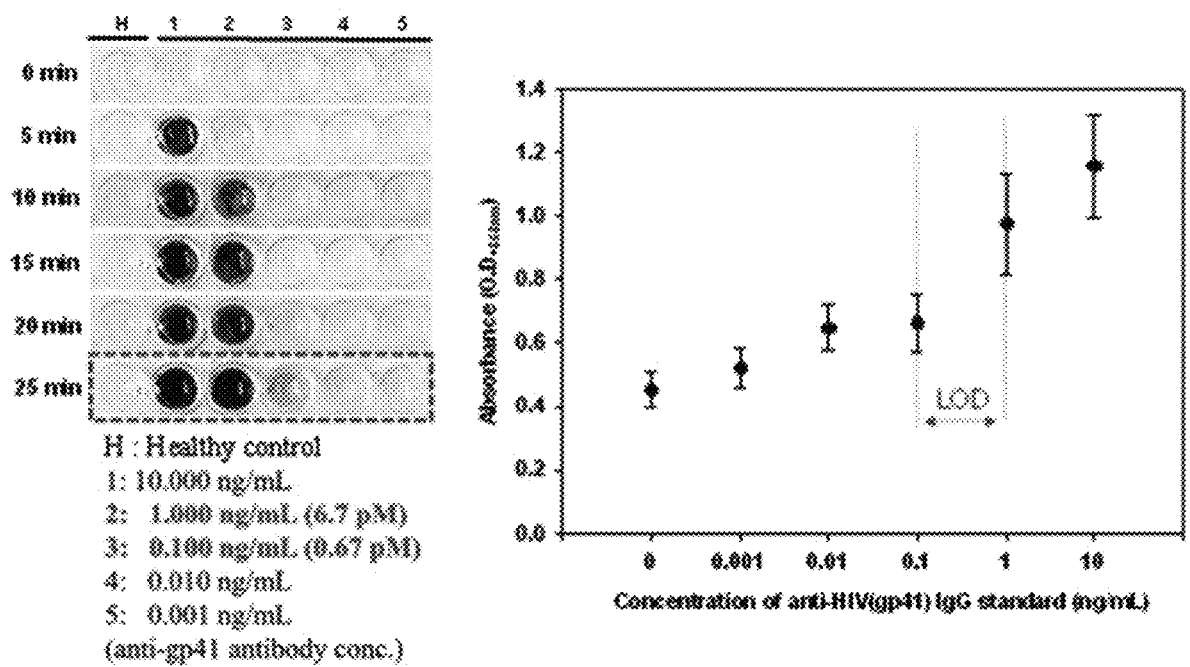
FIG. 28 illustrates quantification experiment results for evaluating the limit of detection (LOD) when diagnosing AIDS using the method of the present invention.

As results, as shown in FIG. 28, it was confirmed that the LOD of the anti-HIV antibody in AIDS was present in a concentration range of at least 0.1 ng/ml (0.67 pM) and at most 1.0 ng/ml (6.7 pM). This was significantly low than the LOD (nM level) of the ELISA-based diagnosis equipment.

As described above, specific portions of the present invention have been described in detail. Those skilled in the art will appreciate that these specific descriptions are merely preferred embodiments, and thus the scope of the present invention is not limited thereto. Therefore, the substantial scope of the present invention will be defined by the appended claims and their equivalents.

A method of detecting a disease-specific marker according to the present invention can diagnose a disease in a single step without any processes such as immobilization and washing processes that are generally accompanied in existing diagnosis methods such as ELISA; can short the time of a diagnostic test, which takes several hours or even several days, to about 10 minutes, thus being effectively used for diagnosis of diseases, in particular, of patients in an emergency; and can be confirmed by the naked eye without a separate analyzer, thus minimizing detection costs.

The invention claimed is:

1. A method of detecting a disease-specific marker using self-amplification of a detection signal, the method comprising:
 (a) a step of simultaneously inducing an antigen-antibody immune reaction and an Au particle formation reaction by reduction of Au ions in an assay solution by, to a pre-assay solution comprising protein particles exposing antibodies or antigens for detection of a disease-specific marker and tags capable of absorbing Au ions on outer surfaces of the protein particles, free Au ions, and Au ions absorbed to the tags, adding a sample, which contains a disease-specific antigen or antibody binding specifically to the antibodies or the antigens, and a reducing agent; and
 (b) a step of confirming the presence or absence of a disease-specific marker by a chromogenic reaction through the Au particle formation.

2. A method of providing information for disease diagnosis using self-amplification of a detection signal, the method comprising:
 (a) a step of simultaneously inducing an antigen-antibody immune reaction and an Au particle formation reaction by reduction of Au ions in an assay solution by, to a pre-assay solution comprising protein particles exposing antibodies or antigens for detection of a disease-specific marker and tags capable of absorbing Au ions on outer surfaces of the protein particles, free Au ions, and Au ions absorbed to the tags, adding a sample, which contains a disease-specific antigen or antibody binding specifically to the antibodies or the antigens, and a reducing agent; and
 (b) a step of confirming the presence or absence of a disease-specific marker by a chromogenic reaction through the Au particle formation.

3. The method according to claim 1, wherein the tags comprises amino acid selected from the group consisting of histidine, lysine, and arginine.

4. The method according to claim 1, wherein the reducing agent is selected from the group consisting of ascorbic acid, imidazole, pyrazole, histamine, hydroxyl amine, citric acid, and sodium borohydride.

5. The method according to claim 1, wherein the sample is selected from the group consisting of blood, plasma, serum, urine, saliva, oral mucosa, and saliva.

6. The method according to claim 1, wherein a concentration of the Au ions present in the pre-assay solution is 1 mM to 10 mM.

7. The method according to claim 1, wherein a concentration of the reducing agent present in the assay solution is 0.005 M to 0.1 M.

8. The method according to claim 1, wherein an amount of the sample is 10 µl to 30 µl.

9. The method according to claim 1, wherein the disease-specific marker is selected from the group consisting of acute heart disease-specific marker, human immunodeficiency syndrome-specific marker, hepatitis C-specific marker, Sjogren's syndrome-specific marker, multiple sclerosis syndrome-specific marker, hepatitis A-specific marker, stroke-specific marker, and cerebral hemorrhage-specific marker.

10. The method according to claim 1, wherein the chromogenic reaction occurs within at least 5 minutes to 10 minutes.

11. The method according to claim 1, wherein the chromogenic reaction is confirmed by measuring an absorbance at 500 to 600 nm.

12. The method according to claim 1, wherein an immune reaction of the antigen or antibody for detecting the disease-specific marker occurs on surfaces of protein particles.

13. The method according to claim 1, wherein the tags adsorbs Au ions to induce aggregation of the Au particles in a presence of the reducing agent.

14. The method according to claim 13, wherein the protein particles comprises a protein selected from the group consisting of ferritin, magnetosome- constituting proteins, virus-constituting proteins, DPS, and proteasome.

* * * * *